United States Patent
Thiele et al.

(10) Patent No.: US 11,402,388 B2
(45) Date of Patent: *Aug. 2, 2022

(54) ANTI-MIF IMMUNOHISTOCHEMISTRY

(71) Applicant: Takeda Pharmaceutical Company Limited, Osaka (JP)

(72) Inventors: Michael Thiele, Vienna (AT); Randolf Kerschbaumer, Klosterneuburg (AT); Dirk Voelkel, Vienna (AT); Patrice Douillard, Vienna (AT); Friedrich Scheiflinger, Vienna (AT); Alexander Schinagl, Vienna (AT)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/414,082

(22) PCT Filed: Jul. 9, 2013

(86) PCT No.: PCT/EP2013/064461
§ 371 (c)(1),
(2) Date: Jan. 9, 2015

(87) PCT Pub. No.: WO2014/009355
PCT Pub. Date: Jan. 16, 2014

(65) Prior Publication Data
US 2015/0160235 A1 Jun. 11, 2015

Related U.S. Application Data

(60) Provisional application No. 61/778,117, filed on Mar. 12, 2013, provisional application No. 61/719,793, filed on Oct. 29, 2012, provisional application No. 61/669,964, filed on Jul. 10, 2012.

(51) Int. Cl.
*G01N 33/68* (2006.01)
*G01N 1/30* (2006.01)

(52) U.S. Cl.
CPC .......... *G01N 33/6863* (2013.01); *G01N 1/30* (2013.01)

(58) Field of Classification Search
CPC .. G01N 1/30; G01N 33/6863; G01N 2440/20; G01N 2440/34; C07K 16/24; C07K 2317/33; C07K 2317/40; C07K 2317/76
See application file for complete search history.

(56) References Cited

U.S. PATENT DOCUMENTS

| | | | | | |
|---|---|---|---|---|---|
| 5,068,178 | A * | 11/1991 | Nowinski | ........ | G01N 33/56966 435/34 |
| 5,116,734 | A * | 5/1992 | Higgs | ...................... | C12Q 1/26 435/28 |
| 5,519,120 | A * | 5/1996 | Dano | ................. | A61K 39/3955 530/388.1 |
| 6,645,493 | B1 * | 11/2003 | Bucala | .................... | C07K 14/52 424/130.1 |
| 2002/0182210 | A1 * | 12/2002 | Rodriguez | ............. | C07K 16/18 424/141.1 |
| 2003/0235584 | A1 * | 12/2003 | Kloetzer | ............ | A01K 67/0276 424/145.1 |
| 2004/0029825 | A1 * | 2/2004 | Davies | ................. | A61K 31/436 514/44 R |
| 2004/0115745 | A1 * | 6/2004 | Diamandis | ....... | G01N 33/57449 435/7.23 |
| 2007/0004910 | A1 * | 1/2007 | Sexton | .................... | A61P 13/10 530/388.26 |

FOREIGN PATENT DOCUMENTS

| WO | WO 2004/101756 A2 | 11/2004 |
|---|---|---|
| WO | WO 2005/003773 A1 | 1/2005 |
| WO | WO 2009/086920 A1 | 7/2009 |
| WO | WO 2011/138462 A1 | 11/2011 |
| WO | WO 2013/050453 A1 | 4/2013 |
| WO | WO 2013/050457 A1 | 4/2013 |
| WO | WO 2013/156472 A1 | 10/2013 |
| WO | WO 2013/156473 A1 | 10/2013 |

OTHER PUBLICATIONS

Malorny et al., 1986. A monoclonal antibody against an antigen present on mouse macrophages and absent from monocytes. Cell Tissue Res. 243: 421-428.*
Malorny et al., 1988. Immunohistochemical demonstration of migration inhibitory factor (MIF) in experimental allergic contact dermatitis. Clin. Exp. Immunol. 71: 164-170.*
Mokry, 1996. Versatility of immunohistochemical reactions: comprehensive survey of detection systems. Acta Medica 39: 129-140.*
Farr et al., 1981. Immunohistochemistry with enzyme labeled antibodies: a brief review. J. Immunol. Meth. 47: 129-144.*
Lan et al., 1998. Macrophage migration inhibitory factor expression in human renal allograft rejection. Transplantation 66: 1465-1471.*
Rice et al., 2003. Interferon-gamma induces macrophage migration inhibitory factor synthesis and secretion by tubular epithelial cells. Nephrology 8: 156-161.*
Watarai et al., 2000. Posttranslational modification of the glycosylation inhibiting factor (GIF) gene product generates bioactive GIF. Proc. Natl. Acad. Sci. USA 97: 13251-13256.*
Li et al., rAAV vector-mediated sarcoglycan gene transfer in hamster model for limb girdle muscular dystrophy, Gene Therapy, 6, p. 74-82 (1999) (Year: 1999).*
Horobin, R. W., Histochemistry: An Explanatory Outline of Histochemistry and Biophysical Staining, 1982, (4 pages) (Year: 1982).*

(Continued)

*Primary Examiner* — Ellen J Marcsisin
(74) *Attorney, Agent, or Firm* — Morgan, Lewis & Bockius LLP

(57) ABSTRACT

The present invention pertains to the specific detection of MIF, in particular oxMIF, in tissues. A detection method is provided which uses immunohistochemistry and wherein specific anti-oxMIF antibodies are used.

Figure 3:
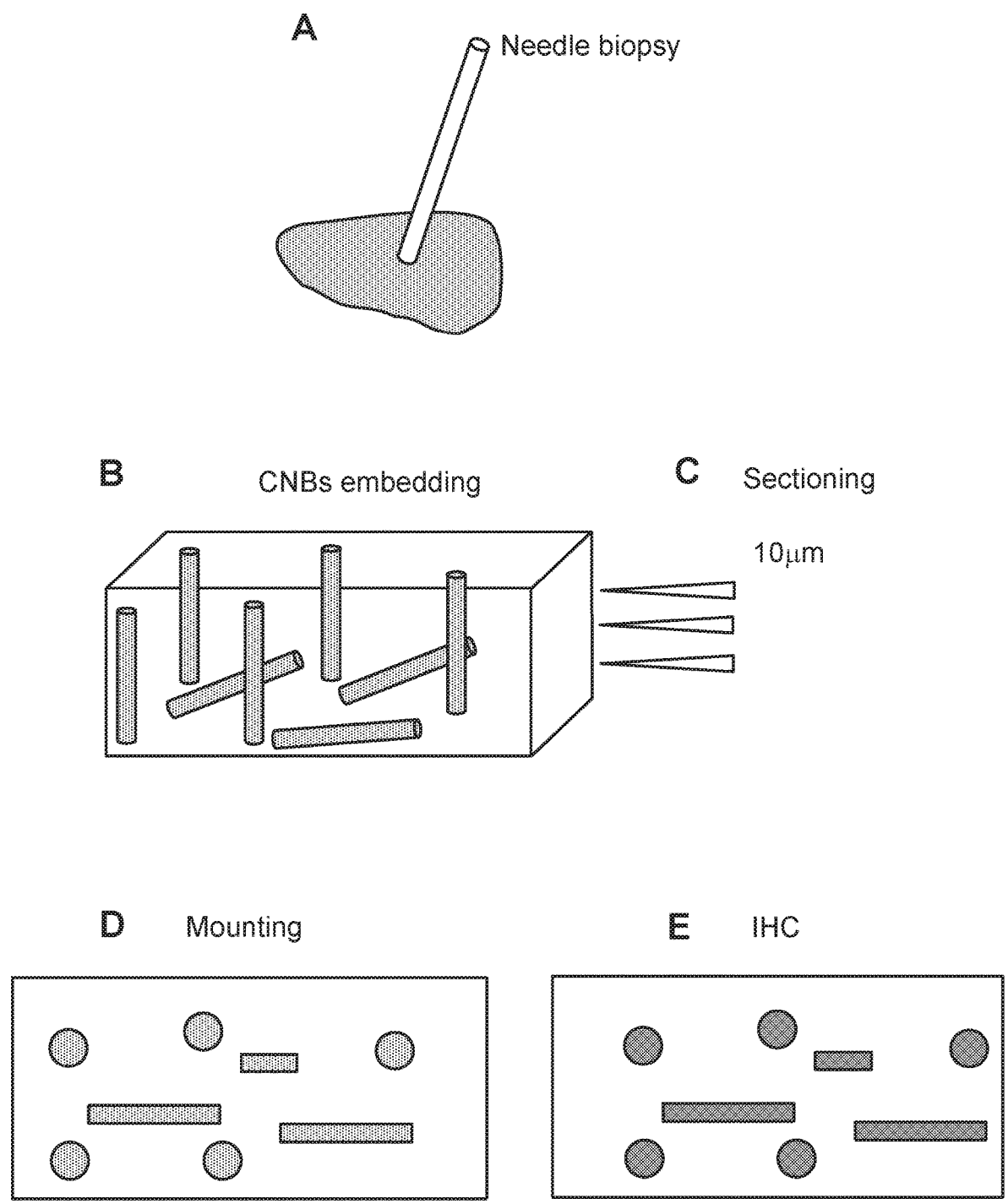

15 Claims, 13 Drawing Sheets
Specification includes a Sequence Listing.

(56) References Cited

OTHER PUBLICATIONS

Molecular Probes, Production Information "Zenon® Rabbit IgG Labeling Kits", (2003) (6 pages) Retrieved from: https://assets.thermofisher.com/TFS-Assets/LSG/manuals/mp25300.pdf on Jan. 6, 2020 (Year: 2003).*
R&D Systems, Tools for Cell Biology Research™, IHC Products & Protocols Guide (2011) (116 pages) (Year: 2011).*
Schinagl et al., Oxidized macrophage migration inhibitory factor is a potential new tissue marker and drug target in cancer, Oncotarget, 7(45), (2016), p. 73486-73496 (Year: 2016).*
International Search Report dated Aug. 21, 2013, for PCT/EP2013/064461, 4 pages.
Angal, S. et al., "A Single Amino Acid Substitution Abolishes the Heterogeneity of Chimeric Mouse/Human (lgG4) Antibody," *Molecular Immunology*, 1993; 30(1): 105-108.
Baugh, J.A et al., "Macrophage migration inhibitory factor," *Crit Care Med*, 2002; 30(1)Suppl.:S27-S35.
Bloom, B.R. et al., "Mechanism of a Reaction in Vitro Associated with Delayed-Type Hypersensitivity," *Science*, Jul. 1, 1966; 153:80-82.
Calandra, T. et al., "MIF as a glucocorticoid-induced modulator of cytokine production," *Nature*, Sep. 7, 1995; 377(7):68-71.
Calandra, T. et al., "Macrophage Migration Inhibitory Factor: A Counter-Regulation of Glucocorticoid Action and Critical Mediator of Septic Shock," *Journal of Inflammation*, 1996; 47:39-51.
David, J.R., "Delayed Hypersensitivity in Vitro: its Mediation by Cell-Free Substances Formed by Lymphoid Cell-Antigen Interaction," *Proc. N.A.S.*, 1966; 56:72-77.
Galat, A. et al., "A diversified family of 12-kDa proteins with a high amino acid sequence similarity to macrophage migration-inhibitory factor (MIF)," *Eur. J. Biochem.*, 1994; 224:417-421.
Kang, Y-S. et al., "Immunoelectron Microscopic Identification of Human NK Cells by FITC-Conjugated Anti-Leu-11a and Biotinylated Anti-Leu-7 Antibodies," *Journal of Immunological Methods*, 1985; 84:177-196.
Kawaguchi, T. et al., "A Monoclonal Antibody Against Migration Inhibitory Factor (MIF) Obtained by Immunization With MIF From the Human Lymphoblast Cell Line Mo," *Journal of Leukocyte Biology*, 1986; 39:223-232.
Lue, H. et al., "Macrophage migration inhibitory factor (MIF) promotes cell survival by activation of the Akt pathway and role for CSN5/JAB1 in the control of autocrine MIF activity," *Oncogene*, 2007; 26:5046-5059.
Mitchell, R.A., "Mechanisms and effectors of MIF-dependent promotion of tumourgenesis," *Cellular Signaling*, 2004; 16:13-19.
Nishihira, J., "Macrophage Migration Inhibitory Factor (MIF): Its Essential Role in the Immune System and Cell Growth," *Journal of Interferon and Cytokine Research*, 2000; 20:751-762.
Shimizu, T. et al., "Identification of macrophage migration inhibitory factor (MIF) in human skin and its immunohistochemical localization," *FEBS Letters*, 1996; 381:199-202.
Sun, H-W. et al., "Crystal structure at 2.6-Å resolution of human macrophage migration inhibitory factor," *Proc. Natl. Acad. Sci. USA*, May 1996; 93:5191-5196.
Watari, H. et al., "Posttranslational modification of the glycosylation inhibiting factor (GIF) gene product generates bioactive GIF," *PNAS*, Nov. 21, 2000; 97(24):13251-13256.
Weiser, W.Y. et al., "Generation of Human Hybridomas Producing Migration Inhibitory Factor (MIF) and of Murine Hybridomas Secreting Monoclonal Antibodies to Human MIF," *Cellular Immunology*, 1985; 90:167-178.
Weiser, W.Y. et al., "Molecular cloning of a cDNA encoding a human macrophage migration inhibitory factor," *Proc. Natl. Acad. Sci. USA*, Oct. 1989; 86:7522-7526.

\* cited by examiner

Figure 1
Figure 1A
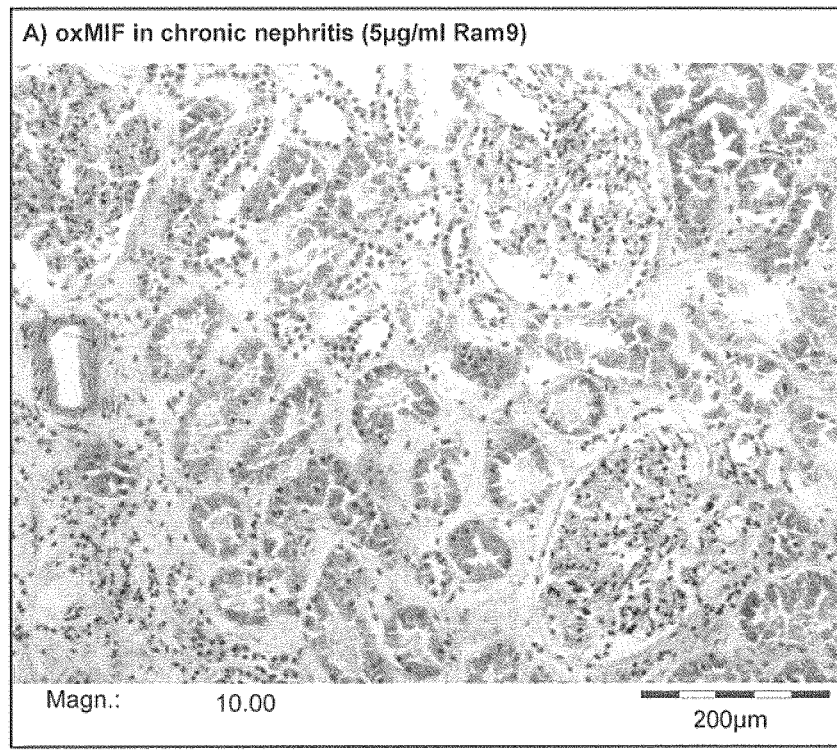
Figure 1B
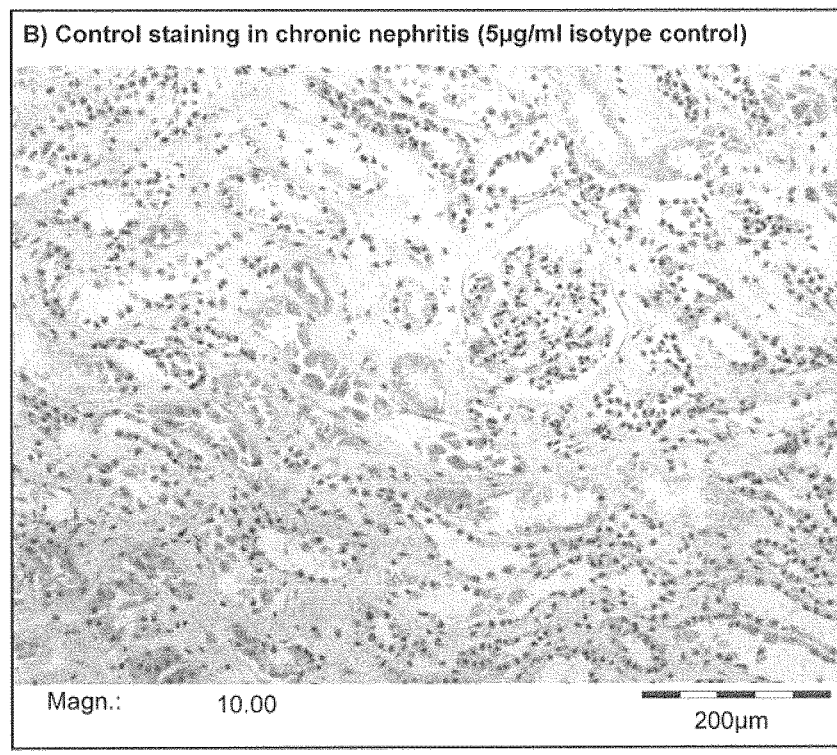

Figure 2
Figure 2A
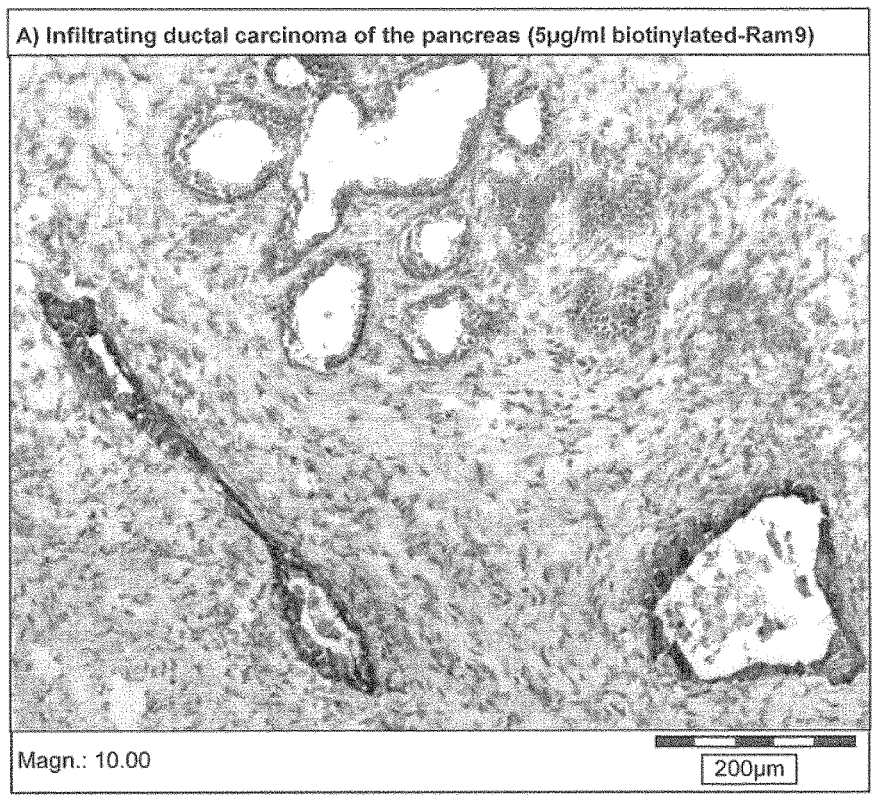
Figure 2B
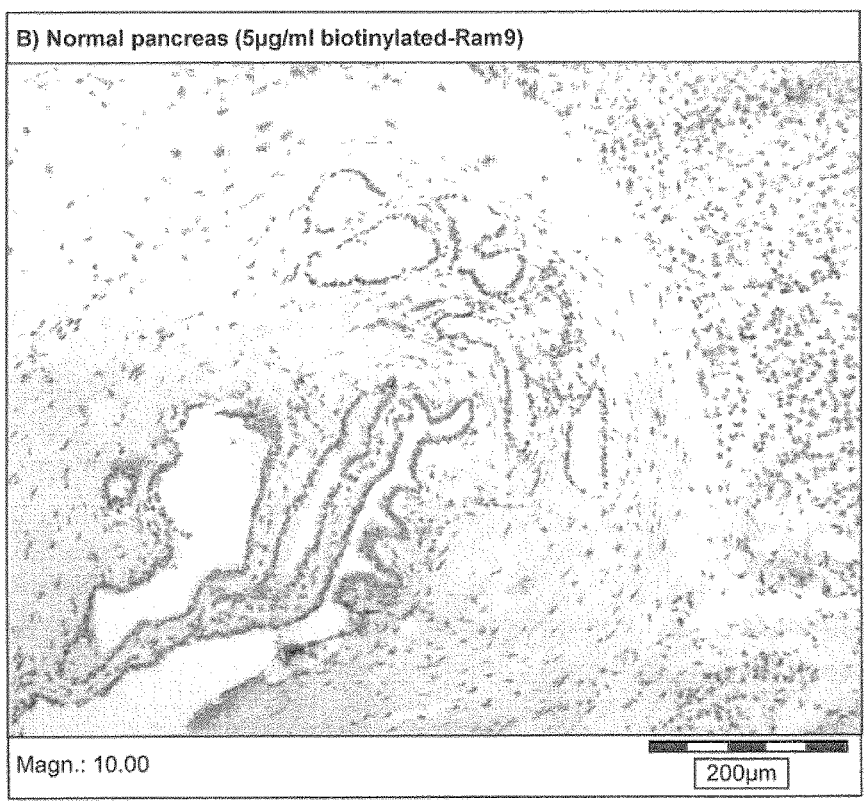

200μm

200μm

SEQUENCE LISTING

<160> NUMBER OF SEQ ID NOS: 14

<210> SEQ ID NO 1
<211> LENGTH: 214
<212> TYPE: PRT
<213> ORGANISM: Artificial Sequence
<220> FEATURE:
<223> OTHER INFORMATION: Light chain of RAB9

<400> SEQUENCE: 1

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Met Thr Tyr
            20                  25                  30

Leu Asn Trp Tyr Gln Gln Lys Pro Gly Lys Ala Pro Lys Leu Leu Ile
        35                  40                  45

Phe Val Ala Ser His Ser Gln Ser Gly Val Pro Ser Arg Phe Arg Gly
    50                  55                  60

Ser Gly Ser Glu Thr Asp Phe Thr Leu Thr Ile Ser Gly Leu Gln Pro
65                  70                  75                  80

Glu Asp Ser Ala Thr Tyr Tyr Cys Gln Gln Ser Phe Trp Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 2
<211> LENGTH: 214
<212> TYPE: PRT
<213> ORGANISM: Artificial Sequence
<220> FEATURE:
<223> OTHER INFORMATION: Light chain of RAB4

<400> SEQUENCE: 2

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 3
<211> LENGTH: 214
<212> TYPE: PRT
<213> ORGANISM: Artificial Sequence
<220> FEATURE:
<223> OTHER INFORMATION: Light chain of RAB0

<400> SEQUENCE: 3

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95
```

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 4
<211> LENGTH: 214
<212> TYPE: PRT
<213> ORGANISM: Artificial Sequence
<220> FEATURE:
<223> OTHER INFORMATION: Light chain of RAB2

<400> SEQUENCE: 4

Asp Ile Gln Met Thr Gln Ser Pro Val Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Thr Pro Arg Leu Leu
        35                  40                  45

Ile Tyr Gly Ala Ser Asn Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Leu
            85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 5

```
<211> LENGTH: 445
<212> TYPE: PRT
<213> ORGANISM: Artificial Sequence
<220> FEATURE:
<223> OTHER INFORMATION: Heavy chain of RAB9

<400> SEQUENCE: 5
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ser Met Asn Trp Val Arg Gln Ala Pro Gly Lys Gly Leu Glu Trp Val
        35                  40                  45

Ser Ser Ile Gly Ser Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Ser Gln Trp Leu Tyr Gly Met Asp Val Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
        420                 425                 430

His Tyr Thr Gln Lys Ser Leu Ser Leu Ser Leu Gly Lys
        435                 440                 445

<210> SEQ ID NO 6
<211> LENGTH: 454
<212> TYPE: PRT
<213> ORGANISM: Artificial Sequence
<220> FEATURE:
<223> OTHER INFORMATION: Heavy chain of RAB4

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Asp Trp Val Arg Gln Ala Pro Gly Lys Gly Leu Glu Trp Val
        35                  40                  45

Ser Gly Ile Val Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

```
Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
            325                 330                 335

Ser Ser Ile Glu Lys Thr Ile Ser Lys Ala Lys Gly Gln Pro Arg Glu
        340                 345                 350

Pro Gln Val Tyr Thr Leu Pro Pro Ser Gln Glu Glu Met Thr Lys Asn
                355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 7
<211> LENGTH: 454
<212> TYPE: PRT
<213> ORGANISM: Artificial Sequence
<220> FEATURE:
<223> OTHER INFORMATION: Heavy chain of RAB0

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ala Met Asp Trp Val Arg Gln Ala Pro Gly Lys Gly Leu Glu Trp Val
        35                  40                  45

Ser Gly Ile Tyr Pro Ser Gly Gly Arg Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205
```

Thr Cys Asn Val Asp His Lys Pro Ser Asn Thr Lys Val Asp Lys Arg
            210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
            325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
            405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 8
<211> LENGTH: 454
<212> TYPE: PRT
<213> ORGANISM: Artificial Sequence
<220> FEATURE:
<223> OTHER INFORMATION: Heavy chain of RAB2

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Asp Trp Val Arg Gln Ala Pro Gly Lys Gly Leu Glu Trp Val
        35                  40                  45

Ser Gly Ile Val Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Lys Thr Tyr
            195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
    275                 280                 285

Val Glu Val His Asn Ala Lys Thr Lys Pro Arg Glu Glu Gln Phe Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Met Thr Lys Asn
    355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
            435                 440                 445

Ser Leu Ser Leu Gly Lys
    450

<210> SEQ ID NO 9
<211> LENGTH: 457
<212> TYPE: PRT
<213> ORGANISM: Artificial Sequence
<220> FEATURE:
<223> OTHER INFORMATION: RAM0hc

<400> SEQUENCE: 9

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Trp Tyr
            20                  25                  30
Ala Met Asp Trp Val Arg Gln Ala Pro Gly Lys Gly Leu Glu Trp Val
        35                  40                  45
Ser Gly Ile Tyr Pro Ser Gly Gly Arg Thr Lys Tyr Ala Asp Ser Val
50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Val Asn Val Ile Ala Val Ala Gly Thr Gly Tyr Tyr Tyr Tyr
            100                 105                 110
Gly Met Asp Val Trp Gly Gln Gly Thr Thr Val Thr Val Ser Ser Ala
        115                 120                 125
Ser Thr Lys Gly Pro Ser Val Phe Pro Leu Ala Pro Ser Ser Lys Ser
130                 135                 140
Thr Ser Gly Gly Thr Ala Ala Leu Gly Cys Leu Val Lys Asp Tyr Phe
145                 150                 155                 160
Pro Glu Pro Val Thr Val Ser Trp Asn Ser Gly Ala Leu Thr Ser Gly
                165                 170                 175
Val His Thr Phe Pro Ala Val Leu Gln Ser Ser Gly Leu Tyr Ser Leu
            180                 185                 190
Ser Ser Val Val Thr Val Pro Ser Ser Ser Leu Gly Thr Gln Thr Tyr
        195                 200                 205
Ile Cys Asn Val Asn His Lys Pro Ser Asn Thr Lys Val Asp Lys Arg
210                 215                 220
Val Glu Pro Lys Ser Cys Asp Lys Thr His Thr Cys Pro Pro Cys Pro
225                 230                 235                 240
Ala Pro Glu Leu Leu Gly Gly Pro Ser Val Phe Leu Phe Pro Pro Lys
                245                 250                 255
Pro Lys Asp Thr Leu Met Ile Ser Arg Thr Pro Glu Val Thr Cys Val
            260                 265                 270
Val Val Asp Val Ser His Glu Asp Pro Glu Val Lys Phe Asn Trp Tyr
        275                 280                 285
Val Asp Gly Val Glu Val His Asn Ala Lys Thr Lys Pro Arg Glu Glu
290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
Ala Leu Pro Ala Pro Ile Glu Lys Thr Ile Ser Lys Ala Lys Gly Gln
            340                 345                 350
Pro Arg Glu Pro Gln Val Tyr Thr Leu Pro Pro Ser Arg Glu Glu Met
        355                 360                 365
Thr Lys Asn Gln Val Ser Leu Thr Cys Leu Val Lys Gly Phe Tyr Pro
370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Lys Leu Thr Val Asp Lys Ser Arg Trp Gln Gln Gly Asn Val
            420                 425                 430
```

Phe Ser Cys Ser Val Met His Glu Ala Leu His Asn His Tyr Thr Gln
            435                 440                 445

Lys Ser Leu Ser Leu Ser Pro Gly Lys
    450                 455

<210> SEQ ID NO 10
<211> LENGTH: 214
<212> TYPE: PRT
<213> ORGANISM: Artificial Sequence
<220> FEATURE:
<223> OTHER INFORMATION: RAM01c

<400> SEQUENCE: 10

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 448
<212> TYPE: PRT
<213> ORGANISM: Artificial Sequence
<220> FEATURE:
<223> OTHER INFORMATION: RAM9hc

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ser Met Asn Trp Val Arg Gln Ala Pro Gly Lys Gly Leu Glu Trp Val
        35                  40                  45

Ser Ser Ile Gly Ser Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Gly Ser Gln Trp Leu Tyr Gly Met Asp Val Trp Gly Gln Gly Thr
        100                 105                 110

Thr Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 12
<211> LENGTH: 214
<212> TYPE: PRT
<213> ORGANISM: Artificial Sequence
<220> FEATURE:

<223> OTHER INFORMATION: RAM91c

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Met Thr Tyr
            20                  25                  30

Leu Asn Trp Tyr Gln Gln Lys Pro Gly Lys Ala Pro Lys Leu Leu Ile
        35                  40                  45

Phe Val Ala Ser His Ser Gln Ser Gly Val Pro Ser Arg Phe Arg Gly
    50                  55                  60

Ser Gly Ser Glu Thr Asp Phe Thr Leu Thr Ile Ser Gly Leu Gln Pro
65                  70                  75                  80

Glu Asp Ser Ala Thr Tyr Tyr Cys Gln Gln Ser Phe Trp Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 457
<212> TYPE: PRT
<213> ORGANISM: Artificial Sequence
<220> FEATURE:
<223> OTHER INFORMATION: RAM4hc

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Asp Trp Val Arg Gln Ala Pro Gly Lys Gly Leu Glu Trp Val
        35                  40                  45

Ser Gly Ile Val Pro Ser Gly Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Val Ile Ala Val Ala Gly Thr Gly Tyr Tyr Tyr Tyr
            100                 105                 110

Gly Met Asp Val Trp Gly Gln Gly Thr Thr Val Thr Val Ser Ser Ala
        115                 120                 125

-continued

```
Ser Thr Lys Gly Pro Ser Val Phe Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Arg
210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
450                 455

<210> SEQ ID NO 14
<211> LENGTH: 214
<212> TYPE: PRT
<213> ORGANISM: Artificial Sequence
<220> FEATURE:
<223> OTHER INFORMATION: RAM41c

<400> SEQUENCE: 14

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Gly Val Ser Ser Ser
            20                  25                  30
```

```
Ser Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Ala Ser Gly Thr Asp Phe Thr Leu Thr Ile Ser Arg Leu Gln
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

ANTI-MIF IMMUNOHISTOCHEMISTRY

CROSS-REFERENCE TO RELATED APPLICATIONS

This application is a 371 application of International Patent Application No. PCT/EP2013/064461, filed on Jul. 9, 2013, which claims the benefit of U.S. Provisional Application No. 61/669,964, filed on Jul. 10, 2012, U.S. Provisional Application No. 61/719,793, filed on Oct. 29, 2012, and U.S. Provisional Application No. 61/778,117, filed on Mar. 12, 2013, the contents of which are incorporated herein by reference in their entireties.

The present invention pertains to the specific detection of MIF, in particular oxMIF, in tissues. A detection method is provided which uses immunohistochemistry and wherein specific anti-oxMIF antibodies are used.

BACKGROUND

Macrophage migration inhibitory factor (MF) is a cytokine initially isolated based upon its ability to inhibit the in vitro random migration of peritoneal exudate cells from tuberculin hypersensitive guinea pigs (containing macrophages) (Bloom et al. Science 1966, 153, 80-2; David et al. PNAS 1966, 56, 72-7). Today, MIF is known as a critical upstream regulator of the innate and acquired immune response that exerts a pleiotropic spectrum of activities. The human MIFcDNA was cloned in 1989 (Weiser et al., PNAS 1989, 86, 7522-6), and its genomic localization was mapped to chromosome 22. The product of the human MIF gene is a protein with 114 amino acids (after cleavage of the N-terminal methionine) and an apparent molecular mass of about 12.5 kDa. MIF has no significant sequence homology to any other protein. The protein crystallizes as a timer of identical subunits. Each monomer contains two antiparallel alpha-helices that pack against a four-stranded beta-sheet. The monomer has additional two beta-strands that interact with the beta-sheets of adjacent subunits to form the interface between monomers. The three subunits are arranged to form a barrel containing a solvent-accessible channel that runs through the center of the protein along a molecular three-fold axis (Sun et al. PNAS 1996, 93, 5191-5196).

It was reported that MIF secretion from macrophages was induced at very low concentrations of glucocorticoids (Calandra et al. Nature 1995, 377, 68-71). However. MIF also counter-regulates the effects of glucocorticoids and stimulates the secretion of other cytokines such as tumor necrosis factor TNF-α and interleukin IL-1 β (Baugh et al., Crit Care Med 2002, 30, S27-35). MIF was also shown e.g. to exhibit pro-angiogenic, pro-proliferative and anti-apoptotic properties, thereby promoting tumor cell growth (Mitchell, R. A., Cellular Signalling, 2004, 16(1): p. 13-19; Lue, H. et al., Oncogene 2007. 26(35): p. 5046-59). It is also e.g. directly associated with the growth of lymphoma, melanoma, and colon cancer (Nishihira et al. J Interferon Cytokine Res. 2000, 20:751-62).

MIF is a mediator of many pathologic conditions and thus associated with a variety of diseases including inter alia inflammatory bowel disease (IBD), rheumatoid arthritis (RA), acute respiratory distress syndrome (ARDS), asthma, glomerulonephritis, IgA nephropathy, myocardial infarction (MI), sepsis and cancer, though not limited thereto. Polyclonal and monoclonal anti-MIF antibodies have been developed against recombinant human MIF (Shimizu et al., FEBS Lett. 1996; 381, 199-202; Kawaguchi et al, Leukoc. Biol. 1986, 39, 223-232, and Weiser et al., Cell. Immunol. 1985, 90, 167-78).

Anti-MFF antibodies have been suggested for therapeutic use. Calandra et al (J. Inflamm. (1995), 47, 39-51) reportedly used anti-MIF antibodies to protect animals from experimentally induced gram-negative and gram-positive septic shock. Anti-MIF antibodies were suggested as a means of therapy to modulate cytokine production in septic shock and other inflammatory disease states.

U.S. Pat. No. 6,645,493 discloses monoclonal anti-MIF antibodies derived from hybridoma cells, which neutralize the biological activity of MIF. It could be shown in an animal model that these mouse-derived anti-MIF antibodies had a beneficial effect in the treatment of endotoxin-induced shock.

US 200310235584 discloses methods of preparing high affinity antibodies to MIF in animals in which the MIF gene has been homozygously knocked-out.

Glycosylation-inhibiting factor (GIF) is a protein described by Galat et al. (Eur. J. Biochem, 1994. 224, 417-21). MIF and GIF are now recognized to be identical. Watarai et al, (PNAS 2000, 97, 13251-6) described polyclonal antibodies binding to different GIF epitopes to identify the biochemical nature of the posttranslational modification of GIF in Ts cells. Watarai et al. supra, reported that GIF occurs in different conformational isoforms in vitro. One type of isomer occurs by chemical modification of a single cysteine residue. The chemical modification leads to conformational changes within the GIF protein.

Elevated MIF levels—i.e., levels of MIF in general—are detected after the onset of various diseases, inter aria after the onset of inflammatory diseases or cancer. However, MIF circulates also in healthy subjects, which makes a clear differentiation difficult. oxMIF, on the contrary, is not present in healthy subjects, oxMIF is increased in disease states and detectable in samples of patients, like e.g. blood, serum and urine.

It has been discovered after thorough research of MIF and antibodies thereto that the antibodies RAB9, RAB4 and RAB0 specifically bind to oxMIF (and are incapable of binding to redMIF).

In earlier experiments carried out by the inventors, it could be shown that oxidative procedures like cystine-mediated oxidation, GSSG (ox. Glutathione)-mediated oxidation or incubation of MIF with Proclin 300 or protein crosslinkers (e.g. BMOE) causes binding of MIF to the above-mentioned antibodies.

The surprising conclusions reached by the present inventors are,
Redox modulation (Cystine/GSSG-mediated mild oxidation) of recombinant MIF (human, murine, rat, CHO, monkey)) or treatment of recombinant MIF with Proclin 300 or protein crosslinkers leads to the binding of Baxter's anti-MIF antibodies RAB9, RAB4 and RAB0
Reduction of oxMIF leads to the loss of Ab binding
Specificity for oxMIF-isoforms correlates with biological Ab efficacy in vivo,
oxMIF levels can be correlated with a disease state.

This additional knowledge regarding (ox)MIF served as a basis for the further studies of the present inventors. So far, no detection method or staining method for the detection of oxMIF in tissue sections exists. It has been shown that the MIF protein exists in different isoforms. The specific detection of native occurring oxMIF, which is considered a strong and reliable marker for MIF related disease states, in tissues, like e.g. tissue sections on glass slides) by immunohistochemistry (in the following also IHC) or immunofluorescence (IF) approaches is hindered by the fact that the structure of oxMIF is influenced or frequently completely lost when standard IHC or IF approaches are applied.

Thus, there is a clear need for a reliable detection method for the oxMIF isoform. This need has been addressed by the present inventors and the goal has been achieved by the invention as described in the following.

SUMMARY OF THE INVENTION

The present invention is directed to a detection method for the detection of oxMIF (ox macrophage migration inhibitory factor). The detection method is based on the principle of an immunohistochemical detection. It is used on tissue samples, in particular tissue sections.

Preferably, these tissue sections are provided on a glass or plastic carrier, e.g. a glass or plastic slide.

The method uses specific oxMIF binding antibodies.

Preferred antibodies for use in the present invention are monoclonal antibodies. In a particularly preferred embodiment, the monoclonal anti-oxMIF antibodies are selected from the group consisting of RAB9, RAB0 and/or RAB4, or from the group consisting of RAM9, RAM0 and/or RAM4, as described in more detail below.

The advantageous specificity of the present method has been shown (see also example section below) by control stainings with isotype control antibodies (which are not able to detect oxMIF and are thus suitable as a negative control) or polyclonal anti-MIF antibodies (which bind to total MIF, consisting of redMIF plus oxMIF, which are suitable as a positive control) and has been further verified by additional findings of the present inventors with the demonstration that oxMIF is detected only in diseased, e.g. cancerous tissue.

The detection method comprises in a preferred embodiment a staining step. This inventive detection/staining protocol itself was designed to conserve the native oxMIF structure in tissue sections. Standard techniques which had been known up to the present invention would lead to a conversion of MIF to oxMIF and would thus give false positive staining in immunohistochemistry techniques.

DETAILED DESCRIPTION OF THE INVENTION

The present invention is, in part, described by the following items:

1. An immunohistochemistry (IHC) assay method for in vitro detection of oxMIF, wherein oxMIF is MIF which is differentially binding to antibody RAB4, RAB9 and/or RAB0 in a tissue sample of a subject, comprising a step of determining binding of a compound to oxMIF in said sample in vitro,
2. The IHC assay of item 1, wherein said compound binding to oxMIF is an antibody, specifically binding to oxMIF.
3. The IHC assay of item 2, wherein the antibody binds to oxMIF, but does not bind to redMIF.
4. The IHC assay of item 3, wherein the differential binding is a binding to oxMIF which occurs with a $K_D$ value of less than 100 nM, preferably less than 50 nM, even more preferred less than 10 nM and a non-binding to redMIF which is characterized by a $K_D$ of more than 400 nM,
5. The IHC assay of any one of items 2 to 4, wherein the antibodies are selected from the group consisting of oxMIF binders, like e.g. antibodies RAB4, RAB9 and/or RAB0 and/or RAM4, RAM9 and/or RAM0.
6. The IHC assay of any of the preceding items, wherein the sample is a tissue biopsy, preferably a frozen tissue biopsy, preferably an OCT embedded section, or a core needle biopsy,
7. The IHC assay of any of the precedings items, wherein one or more of the following steps are carried out:
   a) Optional Blocking step with blocking buffer and
   b) Binding step with primary anti-oxMIF antibody without a previous fixation step;
   c) Optionally fixation step;
   d) Incubation with secondary antibody; and/or
   e) Staining.
8. The IHC assay of any one of the preceding items, wherein no fixation is carried out with an organic or inorganic fixation agent, in particular either formaldehyde or acetone, before the first binding step.
9. The IHC assay of item 7 or 8, wherein the sample is air dried, preferably for about 30 min., after the optional fixation and/or before the first binding step.
10. The IHC assay of any one or more of items 7-9, wherein the primary antibody is biotinylated and/or is preferably comprised in a primary dilution buffer and/or wherein the primary antibody is incubated with the sample preferably for 45 to 90 minutes, more preferred for approximately 60 minutes.
11. The IHC assay of any one or more of items 7-10, wherein a washing step is carried out after incubation step d) to wash away excess antibody.
12. The IHC assay of any one or more of items 7-11, wherein the secondary antibody is a horseradish peroxidase (HRP) conjugated streptavidin.
13. The IHC assay of any one or more of items 7-12, wherein, a washing step is carried out after the incubation step d).
14. The IHC assay of any one or more of items 7-13, wherein the staining step is carried out with hematoxylin.
15. The IHC assay of any one of the preceding items, wherein the binding step is carried out with a biotinylated or fluorescently labelled binding reagent,
16. An IHC assay kit, adapted to carry out the method according to any one or more of the preceding items.

The above mentioned antibodies are characterized and supported by both their sequences as well as by deposits as plasmids in *E. coli* (strain TG1), comprising either the light or the heavy chain of each of the above mentioned antibodies RAB0, RAB4 and RAB9, respectively as well as of RAM0, RAM4 and RAM9, respectively.

The plasmids are characterized by their DSM number which is the official number as obtained upon deposit under the Budapest Treaty with the German Collection of Microorganisms and Cell Cultures (DSMZ), Mascheroder Weg 1b, Braunschweig, Germany. The plasmids were deposited in *E. coli* strains, respectively.

The plasmid with the DSM 25110 number comprises the light chain sequence of the anti-MIF antibody RAB4.

The plasmid with the DSM 25112 number comprises the heavy chain (IgG4) sequence of the anti-MIF antibody RAB4.

The co-expression of plasmids DSM 25110 and DSM 25112 in a suitable host cell results in the production of preferred anti-MIF antibody RAB4.

The plasmid with the DSM 25111 number comprises the light chain sequence of the anti-MIF antibody RAB9.

The plasmid with the DSM 25113 number comprises the heavy chain (IgG4) sequence of the anti-MIF antibody RAB9.

The co-expression of plasmids DSM 25111 and DSM 25113 in a suitable host cell results in the production of preferred anti-MIF antibody RAB9.

The plasmid with the DSM 25114 number comprises the light chain sequence of the anfi-MIF antibody RAB0.

The plasmid with the DSM 25115 number comprises the heavy chain (IgG4) sequence of the anti-MIF antibody RAB0.

The co-expression of plasmids DSM 25114 and DSM 25115 in a suitable host cell results in the production of preferred anti-MIF antibody RAB0.

Also deposited are antibodies RAM0. RAM9 and RAM4; all have been deposited with the DSZM, Braunschweig. Germany on Apr. 12, 2012 according to the Budapest Treaty, with the following designations:

RAM9 heavy chain: *E. coli* GA.662-01.pRAM9hc-DSM 25860,
RAM4 light chain: *E. coli* GA.906-04.pRAM4lc-DSM 25861.
RAM9 light chain: *E. coli* GA.661-01.pRAM9lc-DSM 25859.
RAM4 heavy chain: *E. coli* GA.657-02.pRAM4hc-DSM 25862.
RAM0 light chain: *E. coli* GA.906-01.pRAM0lc-DSM 25863.
RAM0 heavy chain: *E. coli* GA.784-01.pRAM0hc-DSM 25864.

A biological sample in the context of this application in a preferred embodiment, is a tissue sample, preferably a tissue biopsy, a cryo-section of a tissue biopsy (freshly frozen or e.g. OCT embedded), or a core needle biopsy. However, in addition to the above mentioned preferred samples, all further known tissue or cell samples can be used in the present method, as known to a person skilled in the art. OCT embedding in this context refers to an embedding medium for embedding frozen tissue, which is a procedure amply used and well known in the art. OCT stands for Optimal Cutting Temperature, which is ensured by using e.g. this medium. An OCT medium will prevent the formation of freezing artefacts, e.g. destroyal of tissue by water. OCT medium is comprised of 10.24% polyvinyl alcohol, 4.26% polyethylene glycol and 85.50% non-reactive ingredient. This medium, or a similar medium according to general knowledge, is used to embed tissue before sectioning on an e.g. cryostat. Slight variations of this medium will have no influence on the present invention.

The detection of oxMIF in a sample from a patient is an important step for providing a reliable diagnosis of a disease or disorder, in particular to diagnose a patient with being afflicted with a MIF-related disease, i.e. a disease with a participation of (ox)MIF.

The term "prophylactic" or "therapeutic" treatment is art-recognized and refers to administration of a drug to a patient. If a given compound is administered prior to clinical manifestation of the unwanted condition (e.g. disease or other unwanted state of the host, e.g. a human or an animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects thereof).

As used herein an anti-(ox)MIF compound refers to any agent that attenuates, inhibits, opposes, counteracts, or decreases the biological activity of (ox)MIF. An anti(ox)MIF compound may be an agent that inhibits or neutralizes (ox)MIF activity, for example an antibody, particularly preferred, the antibodies as described herein, even more preferred the antibodies RAB9, RAB4 and/or RAB0, or RAM9, RAM4 and/or RAM0.

The present invention is further described by way of figures which are listed herebelow:

FIG. 1A: in situ detection of oxMIF by immunohistochemistry in chronic nephritis FIG. 1B: Control staining in chronic nephritis FIG. 2A: in situ detection of oxMIF by immunohistochemistry in infiltrating ductal carcinoma of the pancreas FIG. 2B: control staining in normal pancreas FIG. 3: schematic overview of breast core-needle biopsy FIG. 4A: in situ detection of oxMIF by IHC in ductal adenocarcinoma, desmoplastic type, stage IB, 48 year old female, Asian with biotinylated RAM9

Figure 4A:
Figure 4B:
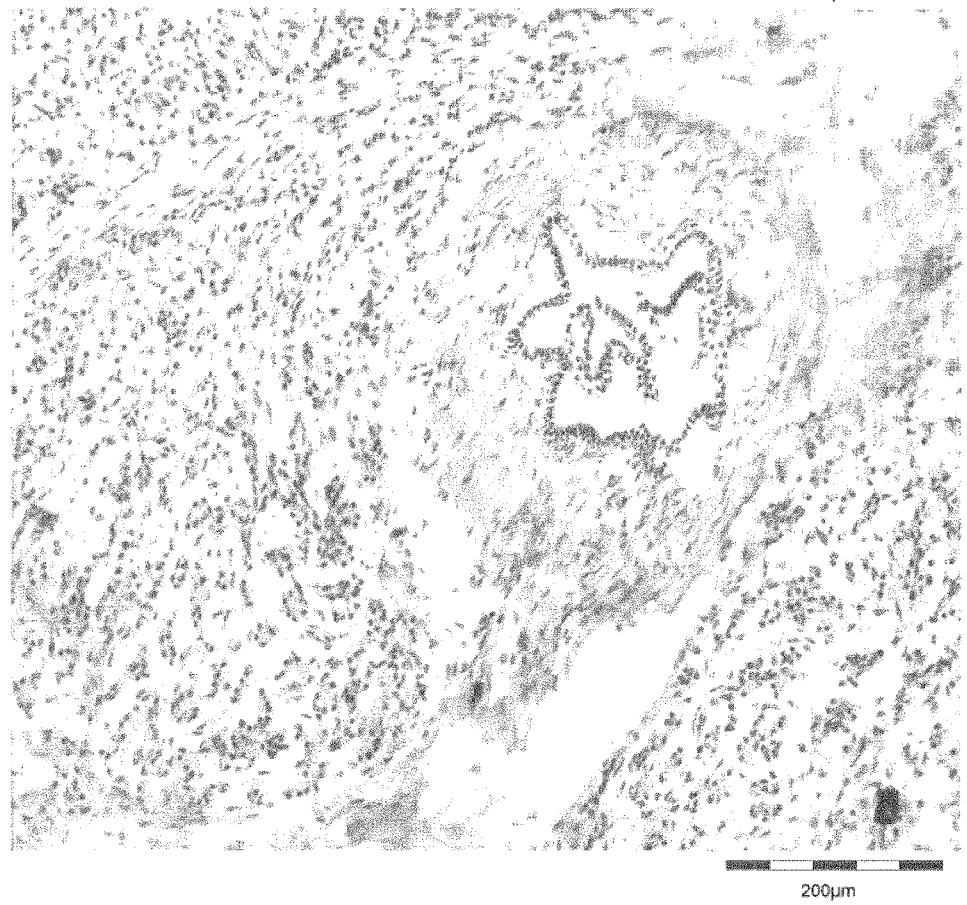
Figure 5A:
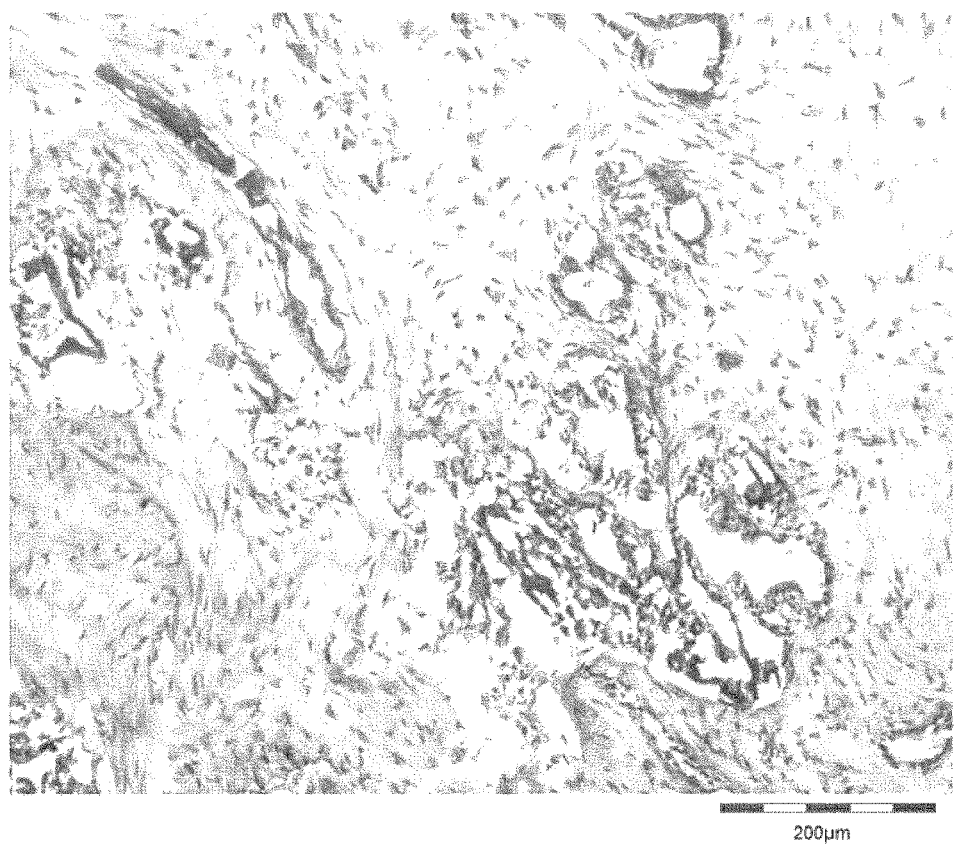

FIG. 4B: in situ detection of oxMIF by IHC in ductal adenocarcinoma, desmoplastic type, stage IB, 48 year old female, Asian with biotinylated control antibody FIG. 5A: in situ detection of oxMIF by IHC in ductal adenocarcinoma, Moderately to poorly differentiated, stage IB, 54 year old male, Asian with biotinylated RAM9

Figure 5B:
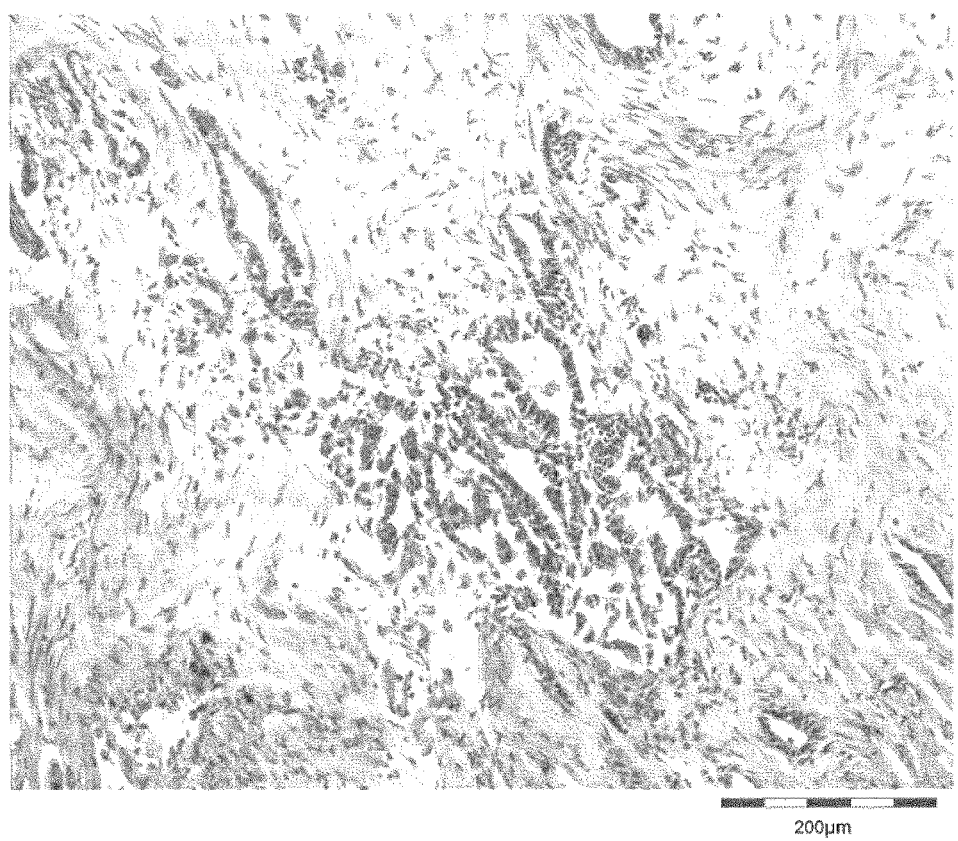
Figure 6:
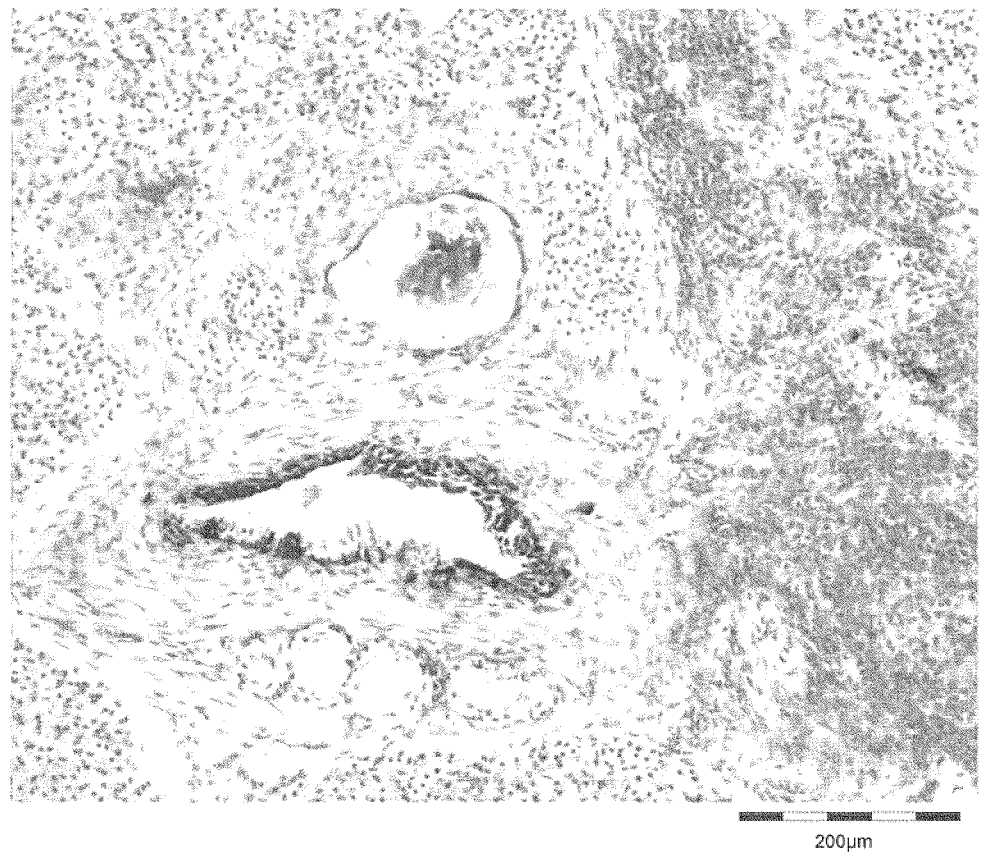

FIG. 5B: in situ detection of oxMIF by IHC in ductal adenocarcinoma, moderately to poorly differentiated, stage IB, 54 year old male, Asian with biotinylated control antibody FIG. 6: in situ detection of oxMIF by IHC in ductal adenocarcinoma, moderately differentiated, stage I, 58 year old patient with biotinylated RAM9

Figure 7A:
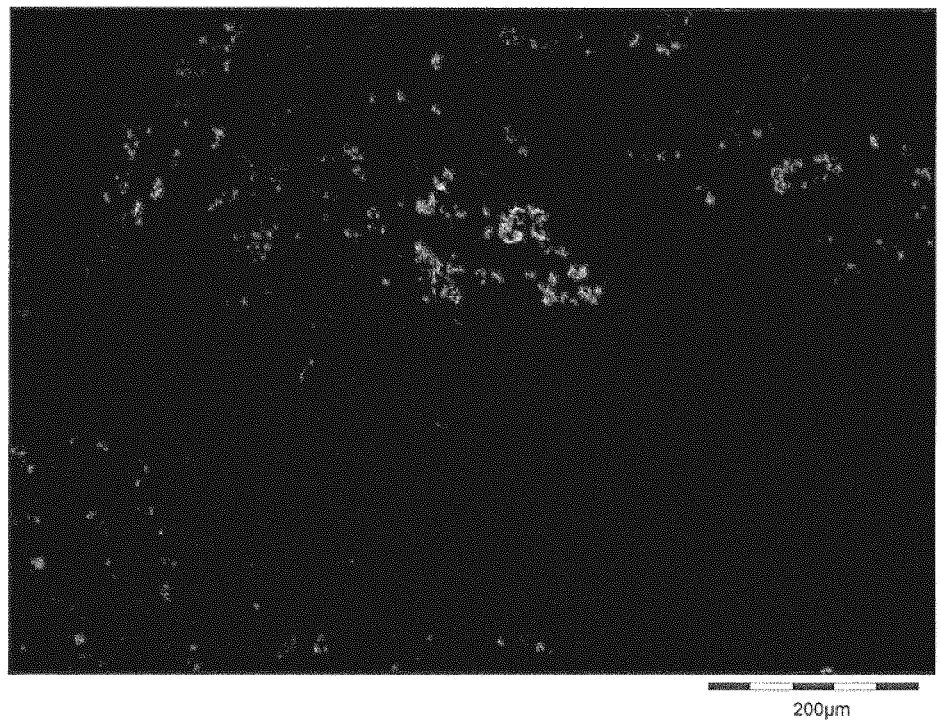
Figure 7B:
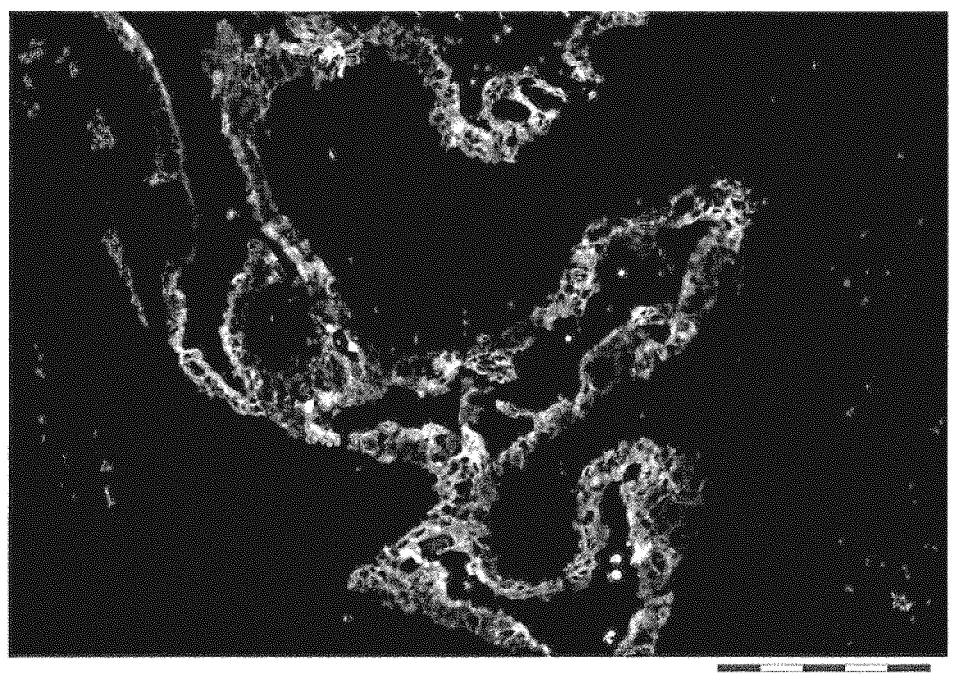

FIG. 7: in situ detection of oxMIF by IF in infiltrating ductal carcinoma, Stage "IIB", 64 year old patient, detection with a fluorescent dye labelled streptavidin
  A: biotinylated control antibody
  B: biotinylated RAM9

Figure 8:
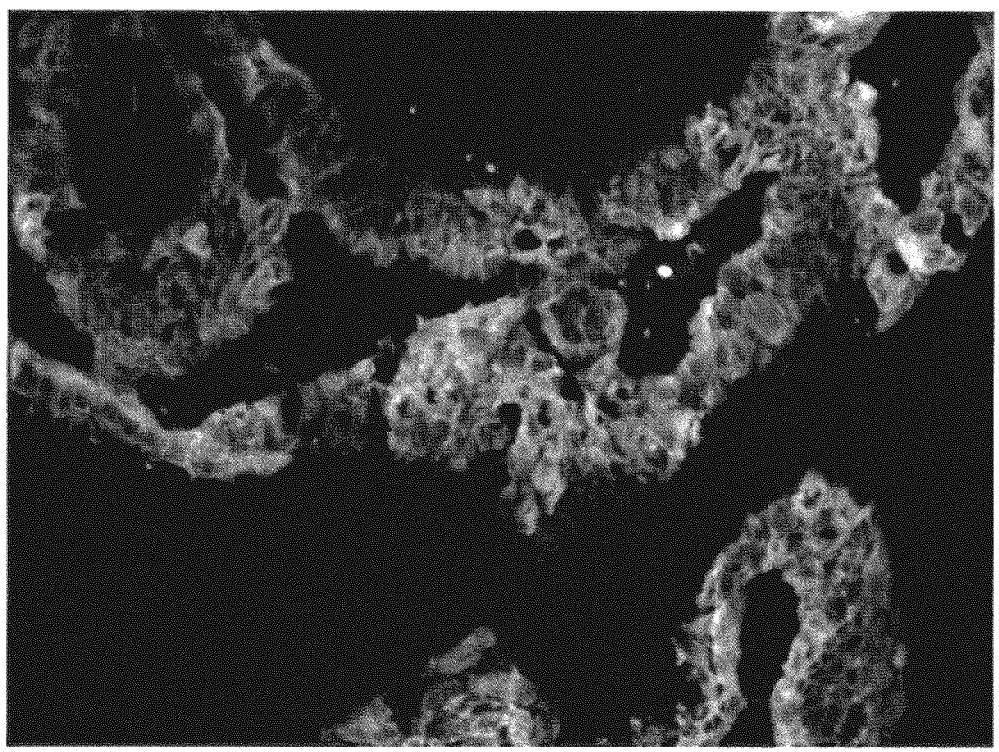
Figure 9A:
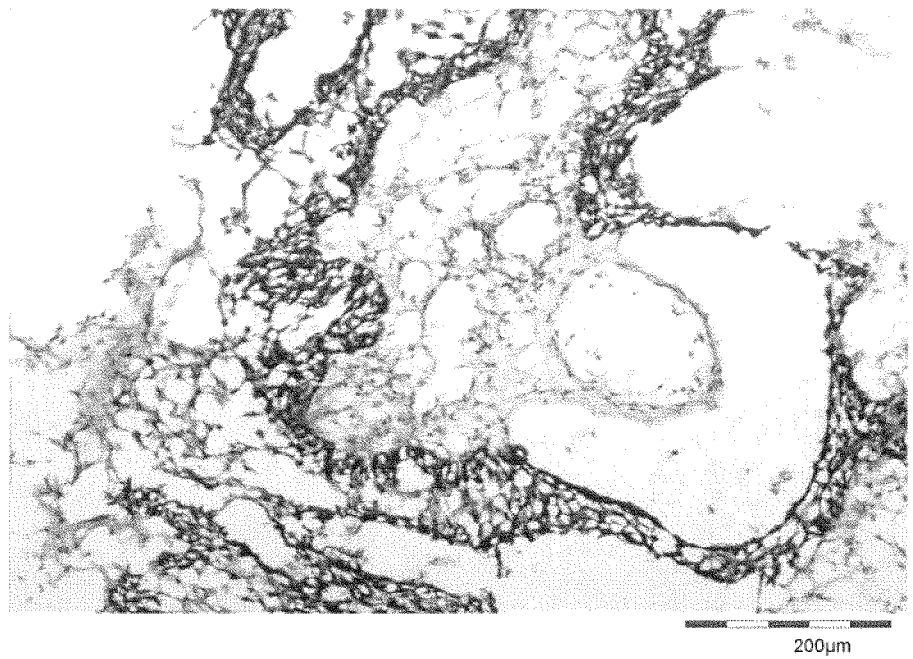
Figure 9B:
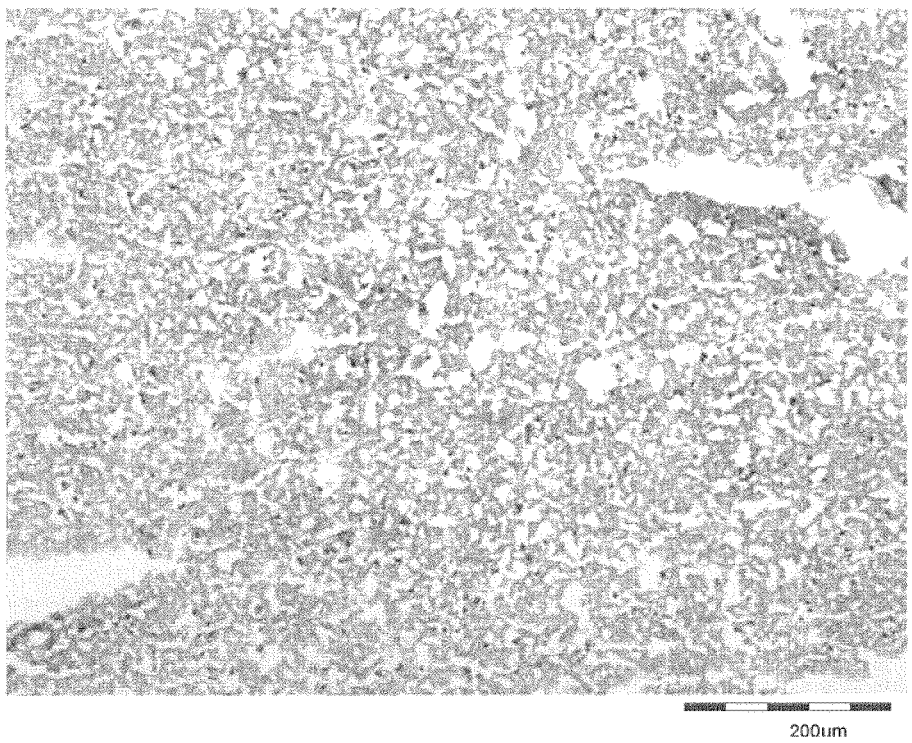
Figure 9C:
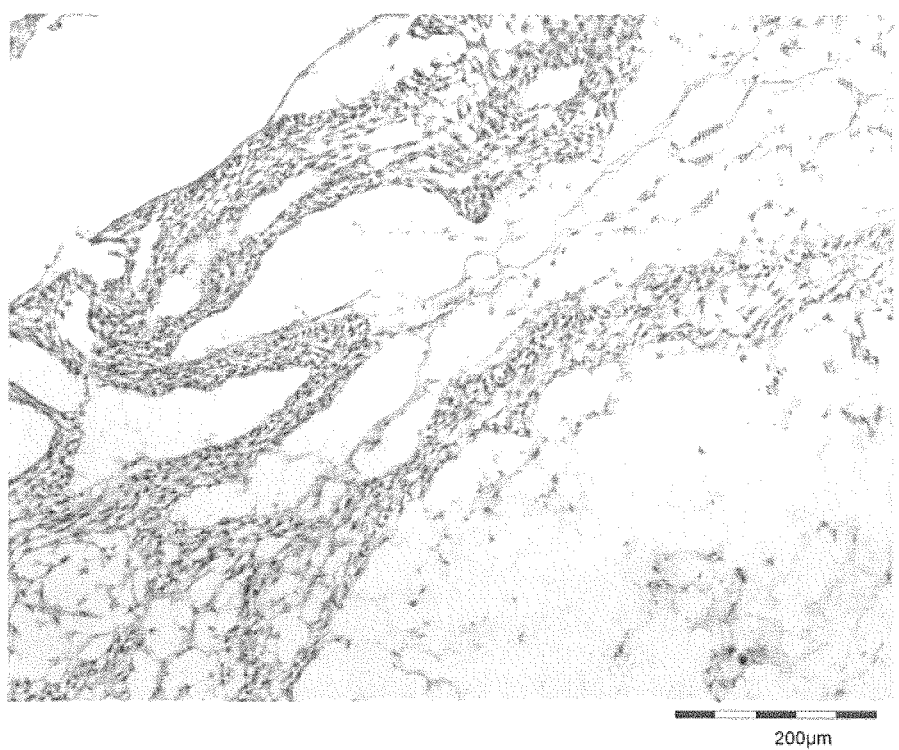
Figure 9D:
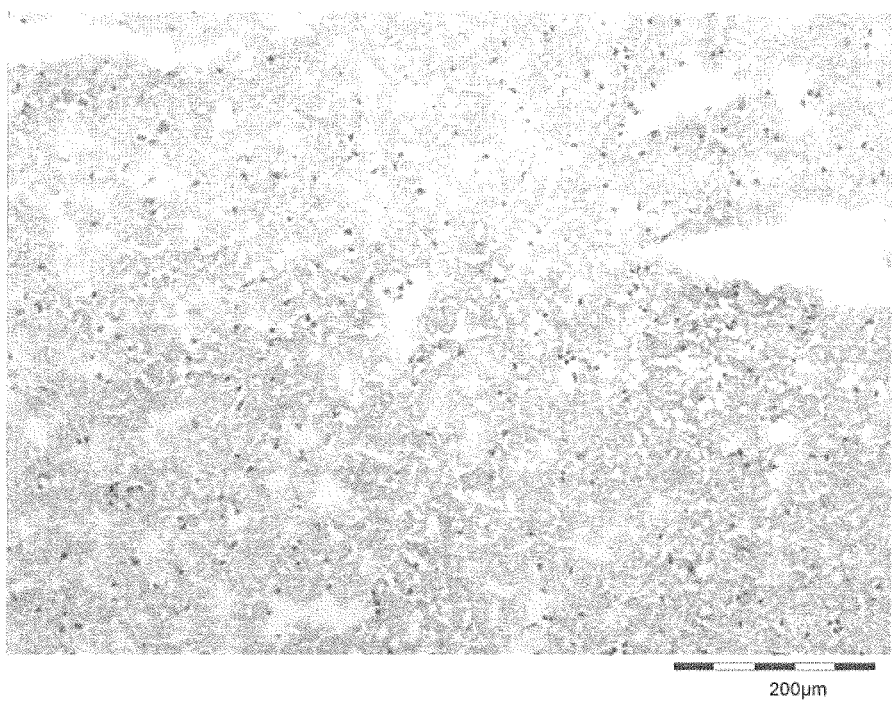

FIG. 8: in situ detection of oxMIF by IF in pancreas, infiltrating ductal adenocarcinoma, stage "IIB", 64 year old patient, detection with directly fluorescent dye labelled RAM9

Figure 10A:
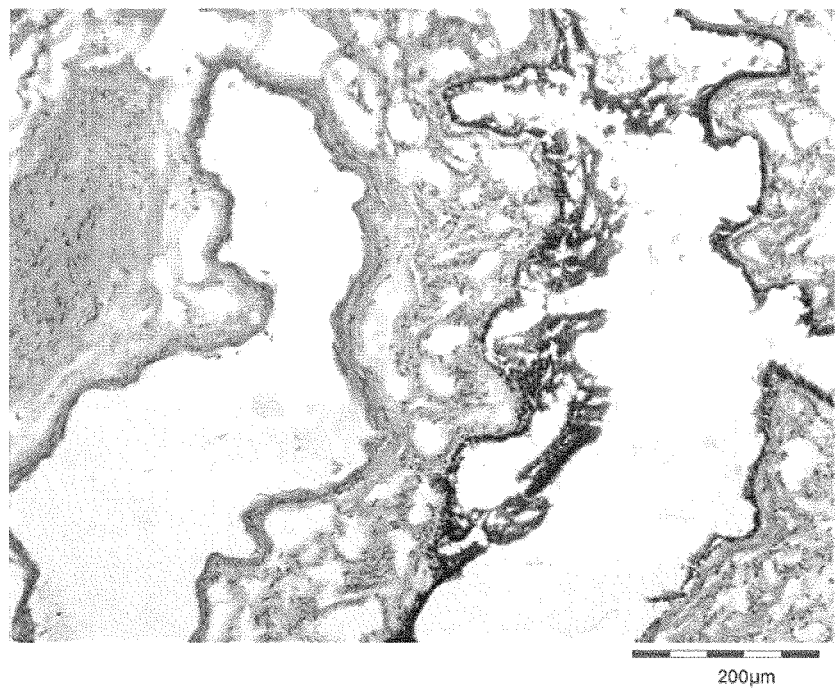
Figure 10:
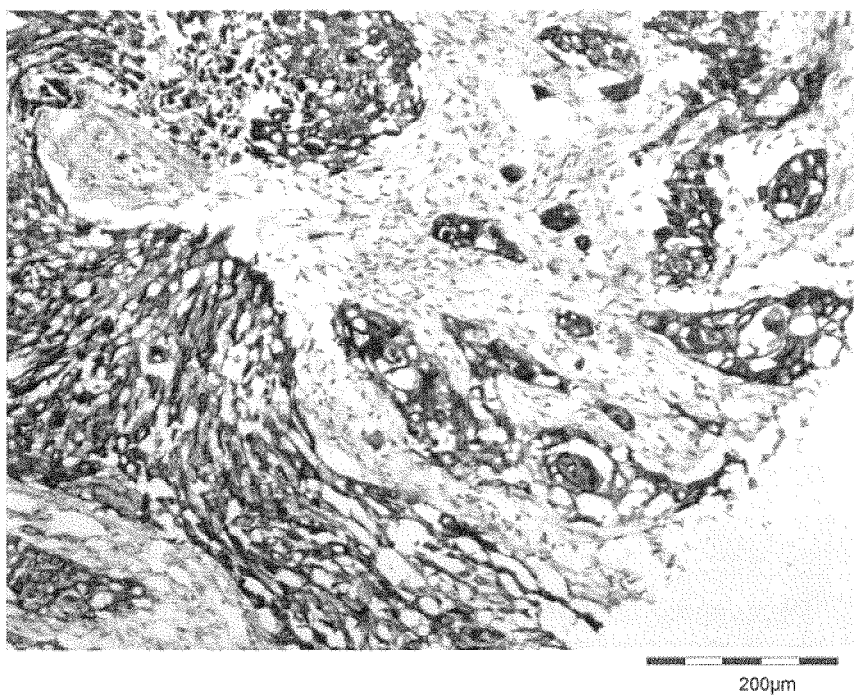
Figure 10C:
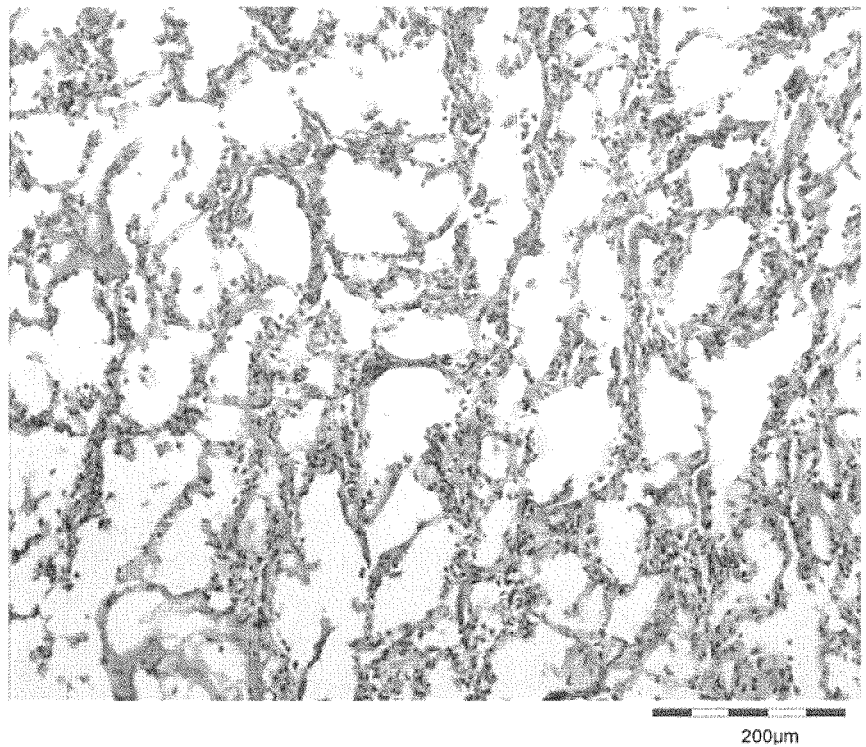
Figure 10D:
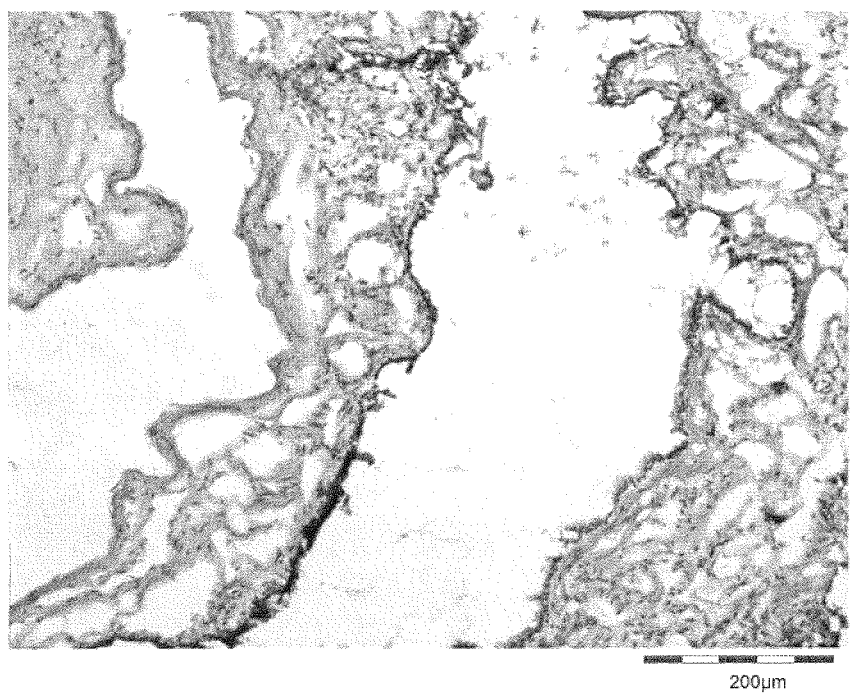
Figure 10E:
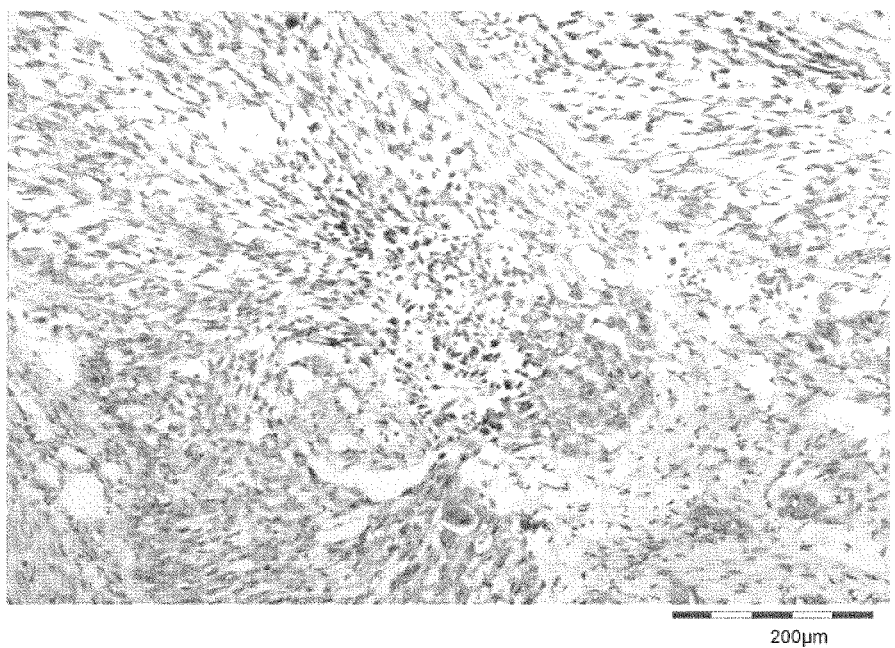
Figure 10F:
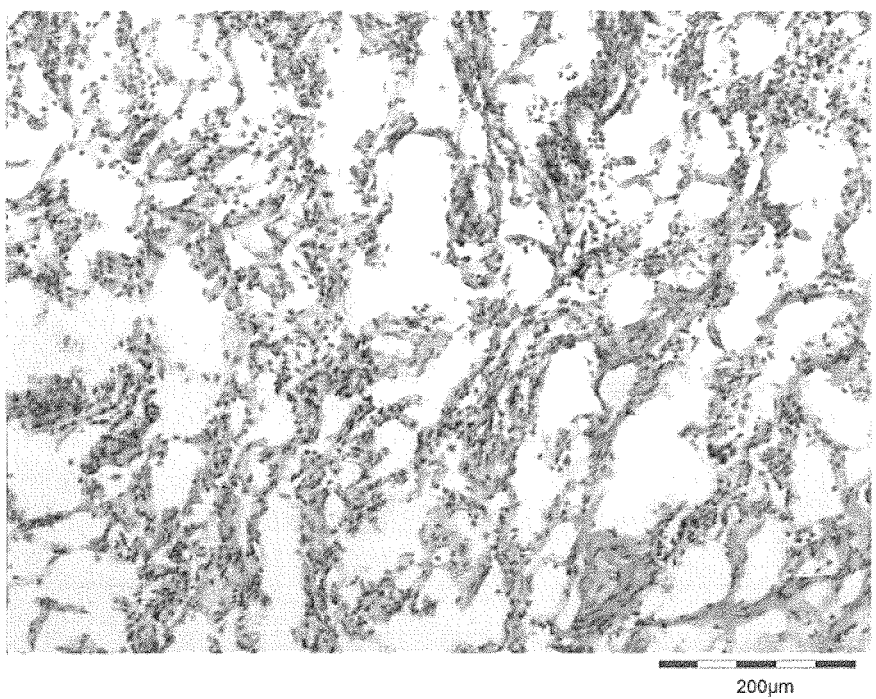

FIG. 9: in situ detection of oxMIF by IHC in brain—craniopharyngioma (32 year old male patient) (patient) and normal brain (60 year old male donor):
  A: biotinylated RAM9/craniopharyngioma
  B: biotinylated RAM9/normal brain
  C: biotinylated control Ab/craniopharyngioma
  D: biotinylated control Ab/normal brain FIG. 10: in situ detection of oxMIF by IHC in lung—adenocarcinoma, papillary (64 year old female patient), squamous cell carcinoma (52 year old male patient) and normal lung (66 year old female donor):
  A: biotinylated RAM9/adenocarcinoma,
  B: biotinylated RAM9/squamous cell carcinoma
  C: biotinylated RAM9/normal lung
  D: biotinylated control Ab/adenocarcinoma
  E: biotinylated control Ab/squamous cell carc.
  F: biotinylated control Ab/normal lung

DEFINITIONS AND GENERAL TECHNIQUES

Unless otherwise defined herein, scientific and technical terms used in connection with the present invention shall have the meanings that are commonly understood by those of ordinary skill in the art. Generally, nomenclatures used in connection with, and techniques of, cell and tissue culture, molecular biology, immunology, microbiology, genetics and protein and nucleic acid chemistry described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al, Molecular Cloning: A Laboratory Manual, 2nd ed., Cold Spring Harbor Laboratory Press, Cold Spring Harbor. N.Y. (1989) and Ausubei et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990), which are incorporated herein by reference.

"MIF" or "macrophage migration inhibitory factor" refers to the protein, which is known as a critical mediator in the immune and inflammatory response, and as a counterregulator of glucocorticoids, MIF includes mammalian MIF, specifically human MIF (Swiss-Prot primary accession number: P14174), wherein the monomeric form is encoded as a 115 amino acid protein but is produced as a 114 amino acid protein due to cleavage of the initial methionine. "MIF" also includes "GIF" (glycosylation-inhibiting factor) and other forms of MIF such as fusion proteins of MIF. The numbering of the amino acids of MIF starts with the N-terminal methionine (amino acid 1) and ends with the C-terminal alanine (amino acid 115).

"oxidized MIF" or oxMIF is defined for the purposes of the invention as an isoform of MIF that occurs by treatment of MIF with mild oxidizing reagents, such as Cystine. As has been shown by the present invention, recombinant oxMIF that has been treated this way comprises isoform(s) of MIF that share structural rearrangements with oxMIF that (e.g.) occurs in vivo after challenge of animals with bacteria.

redMIF is defined for the purposes of this invention as reduced MIF and is MIF which does not bind to RAB0, RAB9 and/or RAB4.

The anti-oxMIF antibodies described in this invention are able to discriminate between ox and redMIF, which are generated by mild oxidation or reduction, respectively, and are useful to specifically detect oxMIF. Discrimination between these conformers is assessed by ELISA or surface plasmon resonance.

Assessing Differential Binding of the Antibodies by Biacore.

Binding kinetics of oxMIF and redMIF to antibody RAB9 and RAB0 are examined by surface plasmon resonance analysis using a Biacore 3000 System. The antibodies were coated on a CM5 (=carboxymethylated dextran) chip and recombinant MIF protein, pre-incubated with 0.2% Proclin 300, were injected, (Proclin 300 consists of oxidative isothiazolones that stabilize the oxMIF structure by avoiding a conversion of oxMIF to redMIF). In native HBS-EP buffer (=Biacore running buffer) without addition of ProClin 300, none of the recombinant MIF proteins bound to RAB9, RAB0 or to the reference antibody (irrelevant isotype control antibody) used as negative (background) binding control.

In a preferred embodiment, oxMIF is MIF which is differentially bound by antibody RAB9. RAB4 and/or RAB0 or an antigen-binding fragment thereof, meaning that these antibodies do bind to oxMIF while redMIF is not bound by either one of these antibodies.

In other embodiments, the anti-oxMIF antibodies, e.g. the antibodies mentioned above or an antigen-binding portion thereof bind oxMIF with a $K_D$ of less than 100 nM, preferably a $K_D$ of less than 50 nM, even more preferred with a $K_D$ of less than 10 nM. Particularly preferred, the antibodies of this invention bind to oxMIF with a $K_D$ of less than 5 nM.

(Non-)binding of an antibody, e.g. RAB9, RAB4 or RAB0 (to oxMIF or redMIF) can be determined as generally known to a person skilled in the art, examples being any one of the following methods: Differential Binding ELISA with recombinant MIF, or surface plasmon resonance using recombinant MIF in its reduced or oxidized state, like the well known Biacore assay, described above.

A preferred method for the determination of binding is surface plasmon resonance of an antibody to e.g. rec. (ox)MIF whereupon "binding" is meant to be represented by a $K_D$ of less than 100 nM preferably less than 50 nM, even more preferred less than 10 nM whereas the non-binding to redMIF is characterized by a $K_D$ of more than 400 nM. "Binding" and "specific binding" is used interchangeably here to denote the above. "Differential binding" in the context of this application means that a compound, in particular the antibodies as described herein, bind to oxMIF (e.g. with the $K_D$ values mentioned above) while they do not bind to redMIF (with non-binding again being defined as above).

An "antibody" refers to an intact antibody or an antigen-binding portion that competes with the intact antibody for (specific) binding. See generally, Fundamental Immunology, Ch. 7 (Paul, W., ed., 2nd ed. Raven Press, N.Y. (1989)) (incorporated by reference). The term antibody includes human antibodies, mammalian antibodies, isolated antibodies and genetically engineered forms such as chimeric, camelized or humanized antibodies, though not being limited thereto.

The term "antigen-binding portion" of an antibody refers to one or more fragments of an antibody that retain the ability to specifically bind to an antigen (e.g. (ox)MIF). Antigen-binding portions may be produced by recombinant DNA techniques or by enzymatic or chemical cleavage of intact antibodies. Antigen-binding portions include e.g.—though not limited thereto—the following: Fab, Fab', F(ab')2, Fv, and complementarity determining region (CDR) fragments, single-chain antibodies (scFv), chimeric antibodies, antibodies and polypeptides that contain at least a portion of an antibody that is sufficient to confer specific antigen binding to the polypeptide, i.e. ox or redMIF. From N-terminus to C-terminus, both the mature light and heavy chain variable domains comprise the regions FR1, CDR1. FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia et al. J. Mol. Biol. 196:901-917 (1987), or Chothia et al., Nature 342:878-883 (1989). An antibody or antigen-binding portion thereof can be derivatized or linked to another functional molecule (e.g., another peptide or protein). For example, an antibody or antigen-binding portion thereof can be functionally linked to one or more other molecular entities, such as another antibody (e.g., a bispecific antibody or a diabody), a detectable agent, a cytotoxic agent, a pharmaceutical agent, and/or a linking molecule.

The term "KD" refers here, in accordance with the general knowledge of a person skilled in the art to the equilibrium dissociation constant of a particular antibody with the respective antigen. This equilibrium dissociation constant measures the propensity of a larger object (here: complex ox or red MIF/antibody) to separate, i.e. dissociate into smaller components (here: ox or redMIF and antibody).

The term "human antibody" refers to any antibody in which the variable and constant domains are human sequences. The term encompasses antibodies with sequences derived from human genes, but which have been changed, e.g. to decrease possible immunogenicity, increase affinity, eliminate cysteines that might cause undesirable folding, etc. The term encompasses such antibodies produced recombinantly in non-human cells, which might e.g. impart glycosylation not typical of human cells.

The term "humanized antibody" refers to antibodies comprising human sequences and containing also on-human sequences.

The term "camelized antibody" refers to antibodies wherein the antibody structure or sequences has been changed to more closely resemble antibodies from camels, also designated camelid antibodies. Methods for the design and production of camelized antibodies are part of the general knowledge of a person skilled in the art.

The term "chimeric antibody" refers to an antibody that comprises regions from two or more different species.

The term "isolated antibody" or "isolated antigen-binding portion thereof" refers to an antibody or an antigen-binding portion thereof that has been identified and selected from an antibody source such as a phage display library or a B-cell repertoire.

The production of the anti-(ox)MIF antibodies according to the present invention includes any method for the generation of recombinant DNA by genetic engineering, e.g. via reverse transcription of RNA and/or amplification of DNA and cloning into expression vectors. In some embodiments, the vector is a viral vector, wherein additional DNA segments may be ligated into the viral genome. In some embodiments, the vector is capable of autonomous replication in a host cell into which it is introduced (e.g. bacterial vectors having a bacterial origin of replication and episomal mammalian vectors). In other embodiments, the vector (e.g. non-episomal mammalian vectors) can be integrated into the genome of a host cell upon introduction into the host cell, and thereby replicated along with the host genome. Moreover, certain vectors are capable of directing the expression of genes to which they are operatively linked. Such vectors are referred to herein as "recombinant expression vectors" (or simply, "expression vectors").

Anti-(ox)MIF antibodies can be produced inter alia by means of conventional expression vectors, such as bacterial vectors (e.g., pBR322 and its derivatives), or eukaryotic vectors. Those sequences that encode the antibody can be provided with regulatory sequences that regulate the replication, expression and/or secretion from the host cell. These regulatory sequences comprise, for instance, promoters (e.g., CMV or SV40 and signal sequences. The expression vectors can also comprise selection and amplification markers, such as the dihydrofolate reductase gene (DHFR), hygromycin-β-phosphotransferase, and thymidine-kinase. The components of the vectors used, such as selection markers, replicons, enhancers, can either be commercially obtained or prepared by means of conventional methods. The vectors can be constructed for the expression in various cell cultures, e.g., in mammalian cells such as CHO, COS, HEK293, NSO, fibroblasts, insect cells, yeast or bacteria such as E. coli. In some instances, cells are used that allow for optimal glycosylation of the expressed protein.

The anti-(ox)MIF antibody light chain gene(s) and the anti-(ox)MIF antibody heavy chain gene(s) can be inserted into separate vectors or the genes are inserted into the same expression vector. The antibody genes are inserted into the expression vector by standard methods, e.g., ligation of complementary restriction sites on the antibody gene fragment and vector, or blunt end ligation if no restriction sites are present.

The production of anti-(ox)MIF antibodies or antigen-binding fragments thereof may include any method known in the art for the introduction of recombinant DNA into eukaryotic cells by transfection, e.g. via electroporation or microinjection. For example, the recombinant expression of anti-(lox)MIF antibody can be achieved by introducing an expression plasmid containing the anti-(ox)MIF antibody encoding DNA sequence under the control of one or more regulating sequences such as a strong promoter, into a suitable host cell line, by an appropriate transfection method resulting in cells having the introduced sequences stably integrated into the genome. The lipofection method is an example of a transfection method which may be used according to the present invention.

The production of anti-(ox)MIF antibodies may also include any method known in the art for the cultivation of said transformed cells, e.g. in a continuous or batchwise manner, and the expression of the anti-(ox)MIF antibody, e.g. constitutive or upon induction. It is referred in particular to WO 2009/086920 for further reference for the production of anti-(ox)MIF antibodies. In a preferred embodiment, the anti-(ox)MIF antibodies as produced according to the present invention bind to oxMIF or an epitope thereof. Particularly preferred antibodies in accordance with the present invention are antibodies RAB9. RAB4 and/or RAB0 as well as RAM9. RAM4 and/or RAM0.

The sequences of these antibodies are partly also disclosed in WO 2009/086920; see in addition the sequence list of the present application and the following:

```
SEQ ID NO: 1 for the amino acid sequence of the fight chain of RAB9:
DIQMTQSPSS LSASVGDRVT ITCRSSQRIM TYLNWYQQKP GKAPKLLIFV ASHSQSGVPS RFRGSGSETD

FTLTISGLQP EDSATYYCQQ SFWTPLTFGG GTKVEIKRTV AAPSVFIFPP SDEQLKSGTA SVVCLLNNFY

PREAKVQWKV DNALQSGNSQ ESVTEQDSKD STYSLSSTLT LSKADYEKHK VYACEVTHQG LSSPVTKSFN

RGEC,

SEQ ID NO: 2 for the amino acid sequence of the light chain of RAB4:
DIQMTQSPGT LSLSPGERAT LSCRASQGVS SSSLAWYQQK PGQAPRLLIY GTSSRATGIP DRFSGSASGT

DFTLTISRLQ PEDFAVYYCQ QYGRSLTFGG GTKVEIKRTV AAPSVFIFPP SDEQLKSGTA SVVCLLNNFY

PREAKVQWKV DNALQSGNSQ ESVTEQDSKD STYSLSSTLT LSKADYEKHK VYACEVTHQG LSSPVTKSFN

RGEC,
```

-continued

SEQ ID NO: 3 for the amino acid sequence of the light chain of RAB0:
DIQMTQSPGT LSLSPGERAT LSCRASQGVS SSSLAWYQQK PGQAPRLLIY GTSSRATGIP DRFSGSASGT

DFTLTISRLQ PEDFAVYYCQ QYGRSLTFGG GTKVEIKRTV AAPSVFIFPP SDEQLKSGTA SVVCLLNNFY

PREAKVQWKV DNALQSGNSQ ESVTEQDSKD STYSLSSTLT LSKADYEKHK VYACEVTHQG LSSPVTKSFN

RGEC,

SEQ ID NO: 4 for the amino acid sequence of the light chain of RAB2:
DIQMTQSPVT LSLSPGERAT LSCRASQSVR SSYLAWYQQK PGQTPRLLIY GASNRATGIP DRFSGSGSGT

DFTLTISRLE PEDFAVYYCQ QYGNSLTFGG GTKVEIKRTV AAPSVFIFPP SDEQLKSGTA SVVCLLNNFY

PREAKVQWKV DNALQSGNSQ ESVTEQDSKD STYSLSSTLT LSKADYEKHK VYACEVTHQG LSSPVTKSFN

RGEC,

SEQ ID NO: 5 for the amino acid sequence of the heavy chain of RAB9:
EVQLLESGGG LVQPGGSLRL SCAASGFTFS IYSMNWVRQA PGKGLEWVSS

IGSSGGTTYY ADSVKGRFTI SRDNSKNTLY LQMNSLRAED TAVYYCAGSQ

WLYGMDVWGQ OTTVIVSSAS TKGPSVFPLA PCSRSTSEST AALGCLVKDY

FPEPVTVSWN SGALTSGVHT FPAVLQSSGL YSLSSVVTVP SSSLGTKTYT

CNVDHKPSNT KVDKRVESKY GPPCPPCPAP EFLGGPSVFL FPPKPKDTLM

ISRTPEVICV VVDVSQEDPE VQFNWYVDGV EVHNAKTKPR EEQFNSTYRV

VSVLTVLHQD WLNGKEYKCK VSNKGLPSSI EKTISKAKGQ PREPQVYTLP

PSQEEMTKNQ VSLTCLVKGF YPSDIAVEWE SNGQPENNYK TTPPVLDSDG

SFFLYSRLTV DKSRWQEGNV FSCSVMHEAL HNHYTQKSLS LSLGK,

SEQ ID NO: 6 for the amino acid sequence of the heavy chain of RAB4:
EVQLLESGGG LVQPGGSLRL SCAASGFTFS IYAMDVVVRQA PGKGLEWVSG

IVPSGGFTKY ADSVKGRFTI SRDNSKNTLY LQMNSLRAED TAVYYCARVN

VIAVAGTGYY YYGMDVWGQG TTVTVSSAST KGPSVFPLAP CSRSTSESTA

ALGCLVKDYF PEPVTVSWNS GALTSGVHTF PAVLQSSGLY SLSSVVTVPS

SSLGTKTYTC NVDHKPSNTK VDKRVESKYG PPCPPCPAPE FLGGPSVFLF

PPKPKDTLMI SRTPEVTCVV VDVSQEDPEV QFNWYVDGVE VHNAKTKPRE

EQFNSTYRVV SVLTVLHQDW LNGKEYKCKV SNKGLPSSIE KTISKAKGQP

REPQVYTLPP SQEEMTKNQV SLTCLVKGFY PSDIAVEWES NGQPENNYKT

TPPVLDSDGS FFLYSRLTVD KSRWQEGNVF SCSVMHEALH NHYTQKSLSL

SLGK,

SEQ ID NO: 7 for the amino acid sequence of the heavy chain of RAB0:
EVQLLESGGG LVQPGGSLRL SCAASGFTFS WYAMDWVRQA PGKGLEWVSG

IYPSGGRTKY ADSVKGRFTI SRDNSKNTLY LQMNSLRAED TAVYYCARVN

VIAVAGTGYY YYGMDVWGQG TTVTVSSAST KGPSVFPLAP CSRSTSESTA

ALGCLVKDYF PEPVTVSWNS GALTSGVHTF PAVLQSSGLY SLSSVVTVPS

SSLGTKTYTC NVDHKPSNTK VDKRVESKYG PPCPPCPAPE FLGGPSVFLF

PPKPKDTLMI SRTPEVTCVV VDVSQEDPEV QFNWYVDGVE VHNAKTKPRE

EQFNSTYRVV SVLTVLHQDW LNGKEYKCKV SNKGLPSSIE KTISKAKGQP

REPQVYTLPP SQEEMTKNQV SLTCLVKGFY PSDIAVEWES NGQPENNYKT

TPPVLDSDGS FFLYSRLTVD KSRWQEGNVF SCSVMHEALH NHYTQKSLSL

SLGK,

-continued

SEQ ID NO: 8 for the amino acid sequence of the heavy chain of RAB2:
EVQLLESGGG LVQPGGSLRL SCAASGFTFS IYAMDWVRQA PGKGLEWVSG IVPSGGFTKY ADSVKGRFTI

SRDNSKNTLY LQMNSLRAED TAVYYCARVN VIAVAGTGYY YYGMDVWGQG TTVTVSSAST KGPSVFPLAP

CSRSTSESTA

ALGCLVKDYF PEPVTVSWNS GALTSGVHTF PAVLQSSGLY SLSSVVTVPS

SSLGTKTYTC NVDHKPSNTK VDKRVESKYG PPCPPCPAPE FLGGPSVFLF

PPKPKDTLMI SRTPEVTCVV VDVSQEDPEV QFNWYVDGVE VHNAKTKPRE

EQFNSTYRVV SVLTVLHQDW LNGKEYKCKV SNKGLPSSIE KTISKAKGQP

REPQVYTLPP SQEEMTKNQV SLTCLVKGFY PSDIAVEWES NGQPENNYKT

TPPVLDSDGS FFLYSRLTVD KSRWQEGNVF SCSVMHEALH NHYTQKSLSL

SLGK,

SEQ ID NO: 9 for the amino acid sequence of RAM0hc:
EVQLLESGGG LVQPGGSLRL SCAASGFTFS WYAMDWVRQA PGKGLEWVSG IYPSGGRTKY ADSVKGRFTI

SRDNSKNTLY LQMNSLRAED TAVYYCARVN VIAVAGTGYY YYGMDVWGQG TTVTVSSAST KGPSVFPLAP

SSKSTSGGTA ALGCLVKDYF PEPVTVSWNS GALTSGVHTF PAVLQSSGLY SLSSVVTVPS

SSLGTKTYTC NVNHKPSNTK VDKRVEPKSC DKTHTCPPCP APELLGGPSV FLFPPKPKDT LMISRTPEVT

CVVVDVSHED PEVKFNWYVD GVEVHNAKTK PREEQYNSTY RVVSVLTVLH QDWLNGKEYK CKVSNKALPA

PIEKTISKAK GQPREPQVYT LPPSREEMTK NQVSLTCLVK GFYPSDIAVE WESNGQPENN

YKTTPPVLDS DGSFFLYSKL TVDKSRWQQG NVFSCSVMHE ALHNHYTQKS LSLSPGK,

SEQ ID NO: 10 for the amino acid sequence of RAM0lc:
DIQMTQSPGT LSLSPGERAT LSCRASQGVS SSSLAWYQQK PGQAPRLLIY GTSSRATGIP DRFSGSASGT

DFTLTISRLQ PEDFAVYYCQ QYGRSLTFGG GTKVEIKRTV AAPSVFIFPP SDEQLKSGTA SVVCLLNNFY

PREAKVQWKV DNALQSGNSQ ESVTEQDSKD STYSLSSTLT LSKADYEKHK VYACEVTHQG LSSPVTKSFN

RGEC,

SEQ ID NO 11 for the amino acid sequence of RAM9hc:
EVQLLESGGG LVQPGGSLRL SCAASGFTFS IYSMNWVRQA PGKGLEWVSS IGSSGGTTYY ADSVKGRFTI

SRDNSKNTLY LQMNSLRAED TAVYYCAGSQ WLYGMDVWGQ GTTVTVSSAS TKGPSVFPLA PSSKSTSGGT

AALGCLVKDY FPEPVTVSWN SGALTSGVHT FPAVLQSSGL YSLSSVVTVP SSSLGTQTYI

CNVNHKPSNT KVDKRVEPKS CDKTHTCPPC PAPELLGGPS VFLFPPKPKD TLMISRTPEV TCVVVDVSHE

DPEVKFNWYV DGVEVHNAKT KPREEQYNST YRVVSVLTVL HQDWLNGKEY KCKVSNKALP APIEKTISKA

KGQPREPQVY TLPPSREEMT KNQVSLTCLV KGFYPSDIAV EWESNGQPEN NYKTTPPVLD SDGSFFLYSK

LTVDKSRWQQ GNVFSCSVMH EALHNHYTQK SLSLSPGK,

SEQ ID NO: 12 for the amino acid sequence of RAM9lc:
DIQMTQSPSS LSASVGDRVT ITCRSSORIM TYLNWYQQKP GKAPKLLIFV ASHSQSGVPS RFRGSGSETD

FTLTISGLOP EDSATYYCQQ SEWTPLTEGG GTKVEIKRTV AAPSVFIFPP SDEQLKSGTA SVVCLLNNFY

PREAKVQWKV DNALQSGNSQ ESVTEQDSKD STYSLSSTLT LSKADYEKHK VYACEVTHQG LSSPVTKSFN

RGEC,

SEQ ID NO: 13 for the amino acid sequence of RAM4hc:
EVQLLESGGG LVQPGGSLRL SCAASGFTFS IYAMDVVRQA PGKGLEWVSG IVPSGGFTKY ADSVKGRFTI

SRDNSKNTLY LQMNSLRAED TAVYYCARVN VIAVAGTGYY YYGMDVWGQG TTVTVSSAST KGPSVFPLAP

SSKSTSGGTA ALGCLVKDYF PEPVTVSWNS GALTSGVHTF PAVLQSSGLY SLSSVVTVPS SSLGTQTYIC

NVNHKPSNTK VDKRVEPKSC DKTHTCPPCP APELLGGPSV FLFPPKPKDT LMISRTPEVT CVVVDVSHED

PEVKFNWYVD GVEVHNAKTK

```
                                                      -continued
PREEQYNSTY RVVSVLTVLH QDWLNGKEYK CKVSNKALPA PIEKTISKAK GQPREPQVYT LPPSREEMTK

NQVSLTCLVK GFYPSDIAVE WESNGQPENN YKTTPPVLDS DGSFFLYSKL TVDKSRWQQG NVFSCSVMHE

ALHNHYTQKS LSLSPGK,

SEQ ID NO: 14 for the amino acid sequence of RAM41c.
DIQMTQSPGT LSLSPGERAT LSCRASQGVS SSSLAWYQQK PGQAPRLLJY GT SRATGIP DRFSGSASGT

DFTLTISRLQ PEDFAVYYCQ QYGRSLTFGG GTKVEIKRTV AAPSVFIFPP SDEQLKSGTA SVVCLLNNFY

PREAKVQWKV DNALQSGNSQ ESVTEQDSKD STYSLSSTLT LSKADYEKHK VYACEVTHQG LSSPVTKSFN

RGEC,
```

The anti-(ox)MIF antibody of the invention is preferably an isolated monoclonal antibody. The anti-MIF antibody can be an IgG, an IgM, an IgE, an IgA, or an IgD molecule. In other embodiments, the anti-MIF antibody is an IgG1, IgG2, IgG3 or IgG4 subclass. In other embodiments, the antibody is either subclass IgG1 or IgG4. In other embodiments, the antibody is subclass IgG4. In some embodiments, the IgG4 antibody has a single mutation changing the serine (serine 228, according to the Kabat numbering scheme) to proline. Accordingly, the CPSC sub-sequence in the Fc region of IgG4 becomes CPPC, which is a sub-sequence in IgG1 (Angel et al. Mol Immunol, 1993, 30, 105-108).

Additionally, the production of anti-(ox)MIF antibodies may include any method known in the art for the purification of an antibody, e.g. via anion exchange chromatography or affinity chromatography. In one embodiment the anti-(ox) MIF antibody can be purified from cell culture supernatants by size exclusion chromatography.

The terms "center region" and "C-terminal region" of MIF refer to the region of human MIF comprising amino acids 35-68 and aa 86-115, respectively, preferably aa 50-68 and aa 86 to 102 of human MIF, respectively.

Particularly preferred antibodies of the present invention bind to either region aa 50-68 or region aa 86-102 of human MIF. This is also reflected by the binding of the preferred antibodies RAB0, RAB4, RAB2 and RAB9 as well as RAM4, RAM9 and RAM0 which bind as follows:
RAB4 and RAM4: aa 86-102
RAB9 and RAM9: aa 50-68
RAB0 and RAM0: aa 86-102
RAB2: aa 86-102

The term "epitope" includes any protein determinant capable of specific binding to an immunoglobulin or an antibody fragment. Epitopic determinants usually consist of chemically active surface groupings of molecules such as exposed amino acids, amino sugars, or other carbohydrate side chains and usually have specific three-dimensional structural characteristics, as well as specific charge characteristics.

The term "vector" refers to a nucleic acid molecule capable of transporting another nucleic acid to which it has been linked. In some embodiments, the vector is a plasmid. i.e., a circular double stranded DNA loop into which additional DNA segments may be ligated.

The term "host cell" refers to a cell line, which is capable to produce a recombinant protein after introducing an expression vector. The term "recombinant cell line", refers to a cell line into which a recombinant expression vector has been introduced. It should be understood that "recombinant cell line" means not only the particular subject cell line but also the progeny of such a cell line. Because certain modifications may occur in succeeding generations due to either mutation or environmental influences, such progeny may not, in fact, be identical to the parent cell, but are still included within the scope of the term "recombinant cell line" as used herein.

The host cell type according to the present invention is e.g. a COS cell, a CHO cell or e.g. an HEK293 cell, or any other host cell known to a person skilled in the art, thus also for example including bacterial cells, like e.g. E. coli cells. In one embodiment, the anti-MIF antibody is expressed in a DHFR-deficient CHO cell line, e.g., DXB11, and with the addition of G418 as a selection marker. When recombinant expression vectors encoding antibody genes are introduced into CHO host cells, the antibodies are produced by culturing the host cells for a period of time sufficient to allow for expression of the antibody in the host cells or secretion of the antibody into the culture medium in which the host cells are grown.

Anti-(ox)MIF antibodies can be recovered from the culture medium using standard protein purification methods. Very surprisingly, the present inventors could show that it was of possible and of particular importance to avoid the state of the art-formaldehyde fixation step before binding. If this fixation was carded out using an (inorganic or organic) solvent, even if using the very well known and usually useful fixation agents formaldehyde or acetone, (which are the most commonly used fixation reagents in the field for tissue sections), the MIF in a sample would tend to change its conformation and false positive results could ensue. This could, though this is a theory only, be the result of this fixation agent/solvent inducing structural rearrangements within the MIF protein to result in structures that resemble oxMIF epitopes.

The inventors could show surprisingly that good and reliable results were obtainable if no fixation step was used before the binding step with the anti-oxMIF antibody. This is contrary to the expectations of a person skilled in the art who would assume that a fixation step is necessary to provide suitable results, as widely confirmed by practically all usually used methods in that field.

In a preferred embodiment of the present invention the sections of the tissue samples should have a thickness of 2 to 15 μm. In a more preferred embodiment these sections have a thickness of 5 to 10 μm.

The biopsies itself were prepared according to state of the art technique known to the person skilled in the art, either fresh frozen or e.g. OCT embedded and sections with the thickness as indicated above were prepared. The steps of the following method and the staining procedure are done at ambient temperature preferably, if not indicated otherwise.

In a preferred embodiment, the sections are air-dried for 20 to 45 minutes, preferably around 30 minutes before the actual procedure starts.

In a preferred embodiment of the method of the present IHC assay, the sample, in particular the tissue sample, is not fixated, in particular not fixated with any inorganic or organic fixation agent or solvent, like formaldehyde or acetone. It is however possible in an optional embodiment to dry the sample before the first binding. It is particularly important that the drying step be carried out in a fashion that avoids oxidation of the sample, and in particular the (ox) MIF presumably comprised therein. Air-drying could be shown by the present inventors to fulfill this requirement. The drying step needs to be carried out without drying components, like e.g. alcoholic components, which have oxidative properties.

In particular, the present inventors could show that by using no fixation procedure before the first binding step (which means also no fixation before the optional blocking step), it is possible to avoid the oxidation of the MIF, using other procedures, it is possible that the MIF structure is re-arranged and thus, would lead to false positive results in the subsequent binding of the antibodies to oxMIF. The samples can however be air-dried before the first binding step.

For the specific binding with the binding compounds of the present invention, preferably the above described anti oxMIF antibodies are used. In a preferred embodiment these antibodies are biotinylated or directly labeled with a fluorescent dye as known in the art. The specific binding can be preceded by use of a blocking buffer in a preferred embodiment which blocks unspecific binding. In an advantageous alternative of this embodiment, the blocking buffer comprises Goat Serum, Serum Albumin and Fish Gelatine in Tris buffered saline (TBS), in a more preferred embodiment 20% Normal Goat Serum, 2% Serum Albumin and 0.2% Fish Gelatine in TBS. In an alternative embodiment the blocking buffer comprises 20% Normal Goat Serum, 2% Bovine Serum Albumin and Gelatine in the Dulbeccos Phosphate Buffered Saline (DPBS). The treatment of the sample with the blocking buffer is preferably carried out for 15 to 45 minutes, very preferably for 30 minutes. It has been shown that if the blocking buffer treatment is carried out for less than 15 minutes the signal/noise ratio will deteriorate, i.e. the background signal relative to the specific signal becomes too high.

Furthermore, in a preferred embodiment the concentration range for the anti oxMIF antibodies is between 0.3 and 20 µg/ml. Particularly advantageous, the concentration range for the anti oxMIF antibody is between 0.5 and 16 µg/ml. Even more preferred, the concentration range for the anti oxMIF antibody is between 5 and 10 µg/ml dilution buffer. Preferably, the sections are fully covered with the oxMIF antibody solution, for which purpose 500 µl solution are sufficient in most cases.

The anti oxMIF antibody is preferably diluted in a primary dilution buffer. In a preferred embodiment this primary dilution buffer comprises Bovine Serum Albumin and Fish Gelatine in TBS, in a more preferred embodiment 2% Bovine Serum Albumin and 0.2% Fish Gelatine in TBS. The incubation with the oxMIF antibody is preferably carried out for 45 to 90 minutes, more preferred for 50-70 minutes, very preferably for approximately 60 minutes. After the binding step, the sections should be dipped shortly in fresh TBS (or e.g. DPBS; washing buffer) to wash away excess antibody; in an alternative embodiment, where the blocking buffer and the dilution buffer used the DPBS instead of TBS the dip should be in fresh DPBS. After the dipping, a washing step in fresh washing buffer should be carried out for approximately 5 to 15 minutes, in a more preferred embodiment for 10 minutes.

As an optional step—which should however be carried out only AFTER the first binding step—it is possible to fix the specimen in a suitable fixation solution, e.g. phosphate buffered formaldehyde, for a time period of 10 to 25 minutes, preferably 15 to 20 minutes. This fixation step with formaldehyde is optional and serves to maintain tissue structures. This step has no negative influence on the (ox) MIF structure and does not lead to false positive results. After this optional step, it is again preferred to dip shortly into TBS (or alternatively DPBS) to wash away excess formaldehyde; the dipping period is as explained above, thereafter it can be incubated for 5-15 min, preferably 10 minutes in fresh TBS (or DPBS, respectively)

Optionally, endogenous peroxidases are then blocked. This can be done by incubating the tissue sections in e.g. $H_2O_2$ in methanol, preferably in 0.3% $H_2O_2$ in methanol for 20-30 minutes. Excess methanol is then preferably removed by washing in TBS for 5-10 minutes.

After these steps, staining in a suitable staining reagent should be carried out according to the preferred embodiment. This staining can be in a preferred embodiment with an HRP conjugated Streptavidin (wherein HRP stands for Horse Radish Peroxidase). Alternatively, other detection methods as known to a person skilled in the art are suitable; e.g. a fluorophore-labelled antibody could be used as a detection tool or the streptavidin could be labelled with a fluorophore. Detection with fluorophore labelled entities has been shown to be suitable by the present inventors in the context of this invention (see e.g. Example 5). This is described in more detail, but generally applicable in example 5, as alternative procedures 1 and 2.

A preferred staining reagent is a VECTASTAIN Elite ABC reagent. The staining period should last at least 20 minutes, preferably at least 30 minutes, in a very preferred embodiment at least 45 minutes.

Preferably, the sections are again dipped shortly in TBS (alternatively DPBS, see above) to wash away excess secondary reagent; thereafter in a preferred embodiment a further incubation for 5 to 15 minutes, preferably 10 minutes in fresh TBS or fresh DPBS is carried out.

The resultant slides are in a preferred embodiment developed with a substrate e.g. a substrate suitable for development using HRP, as well known to a person skilled in the art, e.g. the ImmPACT DAB substrate for 5 to 15 minutes, preferably 10 minutes.

Thereafter, in a preferred embodiment the sections are then shortly dipped in TBS or DPBS see above) to wash away excess substrate and are then incubated for 5 to 15 minutes, preferably 10 minutes in fresh TBS or alternatively DPBS.

After the above step, a counterstaining step to stain the nuclei is preferably carried out; all well known staining agents for immunohistochemistry procedures can be used here. In a preferred embodiment hematoxylin is used. The staining should be carried out for 0.5 to 3 minutes, preferably 1 to 2 minutes.

The sections are thereafter rinsed with tap water and dipped shortly (preferably in tap water again) to wash away excess staining reagent. Thereafter, in an optional embodiment it is incubated for 2 to 6 minutes, preferably 2 to 5 minutes. The incubation time varies and depends on the emergence of the color change form violet to blue in the case of hematoxylin.

For microscopy, the tissue sections are preferably dried, as is well known to a person skilled in the art, in e.g. 70%, following 90%, and absolute ethanol for e.g. 2 min each and afterwards preferably cleared in e.g. Xylene for e.g. at least 3 min. In an alternative embodiment the drying step is done in 96% to absolute ethanol for 2×20 seconds. For long term storage the sections were mounted using VECTASTAIN Permamount and covered with a cover slip. Drying and mounting steps are part of the general knowledge of a person skilled in the art.

The present invention is further explained by way of the following examples, which shall however by no means limit the scope of this invention which is determined by the claims.

EXAMPLES

Example 1 oxMIF in Situ Detection by Immunohistochemistry (IHC) in Kidney from a Chronic Nephritis Patient Cryosections of a kidney from a 67 year old autopsied chronic nephritis patient (glomerulosclerosis as a sub-diagnosis) was obtained commercially. Detection of oxMIF was achieved using biotinylated-RAM9-antibody.
Material and Methods The kidney tissue slides were prepared according to state of the art techniques known to experts, either fresh frozen or OCT embedded, sectioned at 10 µm and stored at <=−80° C. after sectioning. All following steps were done at ambient temperature. The cryo-sections were air dried for 30 min and unspecific binding was blocked with blocking buffer (20% Normal Goat Serum/2% Bovine Serum Albumin/0.2% Fish Gelatine in TBS) for 30 min. The sections were then incubated with a primary, preferably biotinylated, anti-oxMIF Antibody (biotinylated-RAM9) in primary antibody dilution buffer (2% Bovine Serum Albumin/0.2% Fish Gelatine in TBS) at a concentration of 5 µg/ml for 60 min. After washing in TBS, the specimen was fixed in 4% PBS buffered formaldehyde for 15-20 min. Excess formaldehyde was removed by washing in TBS for 10 min. The staining was done using VECTASTAIN Elite ABC Reagent (HRP conjugated Streptavidin) for 30 min. Then the sections were extensively washed again 10 min in TBS. By using ImmPACT DAB Substrate for 10 minutes the staining was visualized as a brown color, which is reflected in FIG. 1A by a dark grey. The slides were washed in TBS and the nuclei were counterstained with Haematoxylin for 1-2 min. By washing the slides in tap water the color of the counter stain changes from violet to blue. For microscopy the tissue sections were dried in 70% following 90% and absolute ethanol for 2 min each and afterwards cleared in Xylene for at least 3 min. For long term storage the sections were mounted using VECTASTAIN Permamount and covered with a cover slip.
Results oxMIF was detected in the kidney from a chronic nephritis patient, with a main staining in the tubules (dark grey in FIG. 1A), as compared to its isotype control (Synagis® antibody, human IgG1) where no staining was observed (FIG. 1B). Only very few RAM9-stained cells were observed in the glomeruli. The blue, (i.e. dot-like in the FIGS. 1A and B attached) structures observed in the sections are nuclei from the cells (hematoxylin staining). To be noted, no oxMIF was detected in the cryosections from a normal kidney when the staining using the same conditions was performed.

Conclusion

In diseased organs such as a kidney from a chronic nephritis patients, oxMIF can be detected in situ by means of IHC techniques, whereas it is absent from a normal kidney.

Example 2 oxMIF in Situ Detection by Immunohistochemistry (IHC) in Pancreas from Infiltrating Ductal Carcinoma Patient Cryosections of both a biopsy from a 64 year old infiltrating ductal carcinoma patient and a biopsy of the healthy part of pancreatic tissue from a 58 year old infiltrating ductal carcinoma patient were obtained commercially. Detection of oxMIF was achieved using biotinylated-RAM9.
Material and Methods The pancreatic tissue biopsy slides were prepared according to state of the art techniques known to experts, either fresh frozen or OCT embedded sectioned at 4-16 µm and stored at <=−80° C. after sectioning. All following steps were done at ambient temperature. The cryo-sections were air dried for 30 min and unspecific binding was blocked with blocking buffer (20% Normal Goat Serum/2% Bovine Serum Albumin 0.2% Fish Gelatine in TBS) for 30 min. The sections were then incubated with a primary, preferably biotinylated, anti-oxMIF Antibody (biotinylated-RAM9) in primary antibody dilution buffer (2% Bovine Serum Albumin/0.2% Fish Gelatine in TBS) at a concentration of 5 µg/ml for 60 min. After washing in TBS, the specimen was fixed in 4% PBS buffered formaldehyde for 15-20 min. Excess formaldehyde was removed by washing in TBS for 10 min. The staining was done using VECTASTAIN Elite ABC Reagent (HRP conjugated Streptavidin) for 30 min. Then the sections were extensively washed again 10 min in TBS. By using ImmPACT DAB Substrate for 10 minutes the staining was visualized as a brown color (dark grey in the attached FIG. 2). The slides were washed in TBS and the nuclei were counterstained with Haematoxylin for 1-2 min. By washing the slides in tap water the color of the counter stain changes from violet to blue. For microscopy the tissue sections were dried in 70% following 90% and absolute ethanol for 2 min each and afterwards cleared in Xylene for at least 3 min. For long term storage the sections were mounted using VECTASTAIN Permamount and covered with a cover slip.
Results oxMIF was detected in the pancreas from a patient suffering infiltrating ductal carcinoma of the pancreas, with a main staining in the PanIN ductal structures (brown staining; i.e. dark grey in FIG. 2A), as compared to normal pancreatic tissue where no staining was observed (FIG. 2B). The blue structures (dot-like in the attached Figure) observed in the sections are the nuclei from the cells (hematoxylin staining). To be noted, no staining was detected in the cryo-sections from normal or cancerous pancreas tissue, when staining was performed using the same conditions with the above mentioned isotype control antibody.

By carrying out additional research the inventors could determine that in a preferred embodiment sections with a thickness of 2 to 16 µm, or 5-10 µm were particularly advantageous. Furthermore, a concentration range for the anti-oxMIF antibody of 0.5 to 16 µg/ml was shown to be particularly advantageous.

Conclusion

In diseased organs such as pancreas from patients suffering infiltrating ductal carcinoma of the pancreas, oxMIF can be detected in situ by means of IHC techniques, whereas it is absent from a healthy pancreatic tissue.

Example 3

Breast Core-Needle Biopsy

One freshly frozen tumor sample (infiltrating lobular carcinoma, Stage IIB, age: 45) or a normal breast sample (adjacent to infiltrating ductal carcinoma, Stage I, age: 43) was partially defrosted. A number of core needle biopsies (CNBs) was taken using a 16 or 18 gauge needle.

The biopsies were embedded into OCT and re-frozen. The resultant product will be a frozen block with CNBs oriented in a mixture of vertical or horizontal positions. Thereafter sections ~10 µm were taken as serial tissue sections per frozen block sample, using a fresh microtome blade per sample. The sections were mounted onto Superfrost Plus glass slides without fixing or mounting medium and stored at <−80° C. (See also FIG. 3).

Material and Methods

The IHC staining was performed as stated in the section "Example 2, Materials and Methods"

Conclusion

In diseases organs such as breast from patients suffering from infiltrating lobular carcinoma of the breast, oxMIF can be detected reliably and in situ by means of IHC technique, whereas it is absent from a healthy pancreatic tissue.

Example 4 oxMIF in Situ Detection by Immunohistochemistry (IHC) in Pancreas from an Infiltrating Ductal Adenocarcinoma of Type IB, in Two Patients In pancreas cancer, the cancer will develop via several stages. Stage IA is the earliest stage of invasive cancer. This cancer is completely inside the pancreas itself. It is smaller than 2 cm and there is no cancer in the lymph nodes or cancer spread (metastases).

Stage IIb (as shown in example 2) designates a cancer where the cancer itself can be any size and may have grown into the tissues surround the pancreas. Cancer is also found in the nearby lymph nodes, but not in the large blood vessels.

Following the same procedure as described for example 2, oxMIF could be detected in the following biopsy samples:

Ductal adenocarcinoma desmoplastic type, stage IB, Sample from a 48 years old Asian woman; the results are shown in FIGS. 4A (RAM9 antibody) and 4B (control antibody)

Ductal adenocarcinoma moderately to poorly differentiated, stage IB, Sample from a 54 years old Asian man; the results are shown in FIGS. 5A (RAM9 antibody) and 5B (control antibody)

Ductal adenocarcinoma moderately differentiated, stage I, Sample from a 58 years old patient; the results are shown in FIG. 6 (RAM9 antibody).

For a comparison with the healthily pancreas, please refer to FIG. 2B.

It can be clearly deduced from these data that it is possible to detect oxMIF already in cancer of an early stage, namely stage I.

Example 5

Alternative Procedure 1 (See Also FIG. 7)

The pancreatic tissue biopsy slides were prepared according to state of the art techniques known to experts, either fresh frozen or OCT embedded, sectioned at 10 µm (4-16 µm), and stored at <=−80° C. after sectioning. All following steps were done at ambient temperature. The cryo-sections were air dried for 30 min (suitable range: 20-30 min) and unspecific binding was blocked with blocking buffer (BB: 20% Normal Goat Serum/2% Bovine Serum Albumin/02% Fish Gelatine in TBS) for 20 min (suitable range: 15-30 min). The sections were then incubated with a primary, preferably biotinylated, Anti-oxMIF Antibody (biotinylated-RAM9) in primary antibody dilution buffer (PADB: 2% Bovine Serum Albumin/0.2% Fish Gelatine in TBS) at a concentration of 5 µg/ml (0.5-16 µg/ml) for 60 min. After washing in TBS, the specimen was fixed in 4% PBS buffered formaldehyde for 20 min (suitable range: 15-30 min). Excess formaldehyde was removed by washing in TBS for 5-10 min. The staining was done by use of fluorescent dye labeled streptavidin 2 µg/ml (suitable range: 1-2.5 µg/ml, namely Streptavidin-Alexa Fluor® 555) diluted in PADB+ 0.25% TritonX-100 for 60 min (suitable range: 30-60 min) in the dark. Slides were then washed in PBST (PBS+0.1% Tween 20) for 10 min (suitable range: 5-10 min). For microscopy, the tissue sections were dried in 96% following absolute ethanol for 2×20 sec each and mounted in Pro-Long® Gold Antifade Reagent with DAPI (nuclear counterstain).

Alternative Procedure 2 (See Also FIG. 8)

The pancreatic tissue biopsy slides were prepared according to state of the art techniques known to experts, either fresh frozen or OCT embedded, sectioned at 10 µm (suitable range: 4-16 µm), and stored at <=−80° C. after sectioning. All following steps were done at ambient temperature. The cryo-sections were air dried for 30 min (suitable range: 20-30 min) and unspecific binding was blocked with blocking buffer (BB: 20% Normal Goat Serum/2% Bovine Serum Albumin/0.2% Fish Gelatine in TBS) for 20 min (suitable range: 15-30 min). The staining was done by use of a directly fluorescent dye labeled RAM9 (e.g. RAM9-Dye-Light®-488) diluted in PADB at a concentration of 10 µg/ml (suitable range: 5-20 µg/ml) for 60 min. After washing in TBS, the specimen was fixed in 4% PBS buffered formaldehyde for 20 min (suitable range: 15-30 min). Excess formaldehyde was removed by washing in PBST (PBS+ 0.1% Tween 20) for 10 min (suitable range: 5-10 min). For microscopy, the tissue sections were dried in 96% following absolute ethanol for 2×20 sec each and mounted in Pro-Long® Gold Antifade Reagent with DAPI (nuclear counterstain)

oxMIF was detected with the above described procedures, namely direct immunofluorescence with a Dye-Light®-488 labeled RAM-9 antibody (Alternative procedure 2; FIG. 8 shows the clear staining and detection of oxMIF) and with an indirect immunofluorescence method using biotinylated antibody and fluorescently labeled streptavidin (Alternative procedure 1; FIG. 7 shows the results).

Example 6

Procedure

The pancreatic tissue biopsy slides were prepared according to state of the art techniques known to experts, either fresh frozen or OCT embedded, sectioned at 4-16 μm, and stored at −80° C. after sectioning. All following steps were done at ambient temperature. The cryo-sections were air dried for 30 min and unspecific binding was blocked with blocking buffer (BB: 20% Normal Goat Serum/2% Bovine Serum Albumin/0.2% Fish Gelatine in TBS) for 20 min (suitable range: 15-30 min). The sections were then incubated with a primary, preferably biotinylated, Anti-oxMIF Antibody (biotinylated-RAM9) in primary antibody dilution buffer (PADB: 2% Bovine Serum Albumin/0.2% Fish Gelatine in TBS) at a concentration of 5 μg/ml (suitable range: 0.5-16 μg/ml) for 60 min, After washing in TBS, the specimen was fixed in 4% PBS buffered formaldehyde for 20 min (suitable range: 15-30 min). Excess formaldehyde was removed by washing in TBS for 10 min. Endogenous peroxidases were blocked by incubating the tissue sections in 0.3% H2O2 in methanol for 20 min (suitable range: 20-30 min). Excess methanol/H2O2 was removed by washing in TBS for 10 min. The staining was done using VEC-TASTAIN Elite ABC Reagent (HRP conjugated Streptavidin) for 30 min (suitable range: 30-45 min). Then the sections were extensively washed again 10 min in TBS. By using ImmPACT DAB Substrate for 5 min (5-10 min) the staining was visualized as a brown color. The slides were washed in TBS and the nuclei were counterstained with Haematoxylin for 1 min (1-2 min). By washing the slides in tab water the color of the counter stain changes from violet to blue. For microscopy the tissue sections were dried in 96% following absolute ethanol for 2×20 sec each and afterwards cleared in Xylene for 2 min (1-5 min). For long term storage the sections were mounted using VEC-TASTAIN Permamount and covered with a cover slip Following this procedure, oxMIF can be differentially detected also in the following tissues:

Brain craniopharyngioma (see also FIGS. 9A-9D)
Lung adenocarcinoma and squamous cell carcinoma (see also FIGS. 10A-10F), as well as
Colon adenocarcinoma.

---

The invention claimed is:

1. An immunohistochemistry (IHC) assay method for in vitro detection of oxidized macrophage migration inhibitory factor (oxMIF), the oxMIF is MIF which is capable of binding to antibodies RAB4, RAB9 and/or RAB0, in a tissue sample of a subject, the IHC assay method comprising a step of determining binding of a primary anti-oxMIF antibody to oxMIF in said sample in vitro, wherein the following steps are carried out:
   a) blocking a sample from a subject with a blocking buffer for at least 15 minutes;
   b) contacting said sample with said primary anti-oxMIF antibody without a previous fixation step, wherein said primary anti-oxMIF antibody binds oxMIF but not reduced macrophage migration inhibitory factor (red-MIF) in vitro, wherein said primary anti-oxMIF antibody is a biotinylated antibody or is unlabeled primary antibody, and wherein said primary anti-oxMIF antibody is incubated with the sample at a concentration of 0.3 g/ml to 20 g/ml for a time period for 45 to 90 minutes;
   c) performing a fixation step, wherein said fixation is carried out in formaldehyde for a time period of 10 to 25 minutes;
   d) incubating with i) a fluorophore labelled streptavidin when the primary antibody is a biotinylated antibody, or ii) a labelled secondary antibody when the primary antibody is unlabeled, thereby labeling oxMIF; and
   e) detecting binding by detecting the label,
   wherein said binding is indicative of the presence of oxMIF in said in vitro sample, and the presence of oxMIF is indicative of the presence of cancer in said sample;
   wherein said primary anti-oxMIF antibody is selected from the group consisting of:
   i. RAM4 antibody, comprising a light chain amino acid sequence of SEQ ID NO: 14 and a heavy chain amino acid sequence of SEQ ID NO: 13,
   ii. RAM9 antibody, comprising a light chain amino acid sequence of SEQ ID NO: 12 and a heavy chain amino acid sequence of SEQ ID NO: 11, and
   iii. RAM0 antibody, which is characterized by a light chain amino acid sequence of SEQ ID NO: 10 and a heavy chain amino acid sequence of SEQ ID NO:9.

2. The IHC assay method of claim 1, wherein the binding to oxMIF occurs with a KD value of less than 100 nM and non-binding to redMIF is characterized by a KD of more than 400 nM.

3. The IHC assay method of claim 1, wherein said sample is a tissue biopsy, a frozen tissue biopsy, an Optimal Cutting Temperature (OCT) embedded section, or a core needle biopsy.

4. The IHC assay method of claim 1, wherein said assay method further comprises a staining step.

5. The IHC assay method of claim 1, wherein said sample is air dried for about 30 minutes, wherein said air drying occurs after said fixation step c) or before said contacting step b).

6. The IHC assay method of claim 1, wherein said primary anti-oxMIF antibody is biotinylated.

7. The IHC assay method of claim 1, further comprising a washing step carried out after said contacting step b) to wash away excess anti-oxMIF antibody.

8. The IHC assay method of claim 4, further comprising a washing step carried out after said incubation step d).

9. The IHC assay method of claim 4, wherein said staining is carried out using hematoxylin, before step e).

10. The IHC assay method of claim 1, wherein said primary anti-oxMIF antibody in said contacting step b) is comprised in a primary dilution buffer.

11. The IHC assay method of claim 1, wherein said primary anti-oxMIF antibody in said contacting step b) is incubated with the sample for approximately 60 minutes.

12. The IHC assay method of claim 1, wherein in step (c) said primary anti-oxMIF antibody is incubated with the sample at a concentration of 0.3 µg/ml to 5 µg/ml for a time period of 45 to 90 minutes.

13. The IHC assay method of claim 1, wherein in step (c) said primary anti-oxMIF antibody is incubated with the sample at a concentration of 0.3 µg/ml to 5 µg/ml for a time period of 45 to 60 minutes.

14. The IHC assay method of claim 1, wherein said fixation step c) is performed with an organic or inorganic fixation agent.

15. The IHC assay method of claim 1, wherein in step (c) said primary anti-oxMIF antibody is incubated with the sample at a concentration of 0.3 µg/ml to 1 µg/ml for a time period of 45 to 55 minutes.

\* \* \* \* \*